United States Patent
Baasov

(10) Patent No.: US 10,786,520 B2
(45) Date of Patent: *Sep. 29, 2020

(54) AMINOGLYCOSIDE DERIVATIVES AND USES THEREOF IN TREATING GENETIC DISORDERS

(71) Applicant: Eloxx Pharmaceuticals Ltd., Rehovot (IL)

(72) Inventor: Timor Baasov, Haifa (IL)

(73) Assignee: ELOXX PHARMACEUTICALS LTD., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/756,591

(22) PCT Filed: Sep. 2, 2016

(86) PCT No.: PCT/IL2016/050966
§ 371 (c)(1),
(2) Date: Mar. 1, 2018

(87) PCT Pub. No.: WO2017/037718
PCT Pub. Date: Mar. 9, 2017

(65) Prior Publication Data
US 2018/0177812 A1    Jun. 28, 2018

Related U.S. Application Data

(60) Provisional application No. 62/213,187, filed on Sep. 2, 2015.

(51) Int. Cl.
| | | |
|---|---|---|
| A61K 31/7036 | (2006.01) | |
| C07H 15/23 | (2006.01) | |
| A61P 21/04 | (2006.01) | |
| A61P 7/04 | (2006.01) | |

(52) U.S. Cl.
CPC ............ *A61K 31/7036* (2013.01); *A61P 7/04* (2018.01); *A61P 21/04* (2018.01); *C07H 15/23* (2013.01)

(58) Field of Classification Search
None
See application file for complete search history.

(56) References Cited

U.S. PATENT DOCUMENTS

| | | |
|---|---|---|
| 3,897,412 A | 7/1975 | Naito et al. |
| 3,978,214 A | 8/1976 | Mallams et al. |
| 3,996,205 A | 12/1976 | Magerlein et al. |
| 4,024,332 A | 5/1977 | Fenner et al. |
| 4,029,882 A | 6/1977 | Wright |
| 4,169,197 A | 9/1979 | Magerlein |
| 4,396,609 A | 8/1983 | Daum et al. |
| 5,096,596 A | 3/1992 | Hellenbrand et al. |
| 5,470,836 A | 11/1995 | Donno et al. |
| 6,541,456 B1 | 4/2003 | Swayze et al. |
| 6,967,242 B2 | 11/2005 | Swayze et al. |
| 8,895,519 B2 | 11/2014 | Baasov et al. |
| 9,175,029 B2 | 11/2015 | Baasov et al. |
| 9,616,079 B2 | 4/2017 | Baasov et al. |
| 10,576,095 B2 | 3/2020 | Baasov et al. |
| 2005/0004052 A1 | 1/2005 | Baasov et al. |
| 2005/0148522 A1 | 7/2005 | Baasov et al. |
| 2018/0265535 A1 | 9/2018 | Baasov |
| 2018/0282361 A1 | 10/2018 | Baasov et al. |
| 2019/0016745 A1 | 1/2019 | Baasov |
| 2019/0016746 A1 | 1/2019 | Baasov et al. |

FOREIGN PATENT DOCUMENTS

| | | |
|---|---|---|
| DE | 3100739 | 8/1982 |
| EP | 1710248 | 10/2006 |
| FR | 2427341 | 12/1979 |
| JP | 04-046189 | 2/1992 |
| JP | 2009-532461 A | 9/2009 |
| JP | 2013-542981 A | 11/2013 |
| KR | 20150137577 A | 12/2015 |
| WO | WO 2004/093821 | 11/2004 |
| WO | WO 2005/002497 | 1/2005 |
| WO | WO 2006/027784 | 3/2006 |
| WO | WO 2006/090382 | 8/2006 |
| WO | WO 2007/113841 | 10/2007 |
| WO | WO 2009/093821 | 7/2009 |
| WO | WO 2010/004433 | 1/2010 |
| WO | WO 2011/044538 | 4/2011 |
| WO | WO 2011/124986 | 10/2011 |
| WO | WO 2012/066546 | 5/2012 |
| WO | WO 2015/186134 | 12/2015 |
| WO | WO 2017/037717 | 3/2017 |
| WO | WO 2017/037718 | 3/2017 |
| WO | WO 2017/037719 | 3/2017 |
| WO | WO 2017/118967 | 7/2017 |
| WO | WO 2017/118968 | 7/2017 |

OTHER PUBLICATIONS

International Preliminary Report on Patentability dated Jul. 19, 2018 From the International Bureau of WIPO Re. Application No. PCT/IL2016/050967. (8 Pages).
International Preliminary Report on Patentability dated Jul. 19, 2018 From the International Bureau of WIPO Re. Application No. PCT/IL2016/050969. (7 Pages).
International Preliminary Report on Patentability dated May 26, 2006 From the International Bureau of WIPO Re. Application No. PCT/IL2004/000490.
International Search Report and the Written Opinion dated Jun. 19, 2006 From the International Searching Authority Re. Application No. PCT/IL2005/000959.
Official Action dated Aug. 1, 2007 From the US Patent and Trademark Office Re. U.S. Appl. No. 11/073,649.
Official Action dated Dec. 15, 2008 From the US Patent and Trademark Office Re. U.S. Appl. No. 11/073,649.

(Continued)

*Primary Examiner* — Samantha L Shterengarts
(74) *Attorney, Agent, or Firm* — Perkins Coie LLP; Patrick D. Morris

(57) ABSTRACT

Novel pseudo-trisaccharide aminoglycosides, represented by Formula I, as defined in the instant specification, designed to exhibit stop codon mutation readthrough activity, are provided. Also provided are pharmaceutical compositions containing the same, and uses thereof in the treatment of genetic diseases and disorders, such as diseases and disorders associated with stop codon mutations.

24 Claims, 3 Drawing Sheets

(56) References Cited

OTHER PUBLICATIONS

Official Action dated Apr. 17, 2008 From the US Patent and Trademark Office Re. U.S. Appl. No. 11/073,649.
Corrected International Search Report and the Written Opinion dated Dec. 18, 2016 From the International Searching Authority Re. Application No. PCT/IL2016/050967. (15 Pages).
International Preliminary Report on Patentability dated Mar. 15, 2017 From the International Bureau of WIPO Re. Application No. PCT/IL2016/050965. (8 Pages).
International Preliminary Report on Patentability dated Mar. 15, 2018 From the International Bureau of WIPO Re. Application No. PCT/IL2016/050966. (7 Pages).
International Preliminary Report on Patentability dated Mar. 15, 2018 From the International Bureau of WIPO Re. Application No. PCT/IL2016/050968. (9 Pages).
International Preliminary Report on Patentability dated Mar. 22, 2007 From the International Bureau of WIPO Re. Application No. PCT/IL2005/000959.
International Search Report and the Written Opinion dated Dec. 6, 2016 From the International Searching Authority Re. Application No. PCT/IL2016/050968. (13 Pages).
International Search Report and the Written Opinion dated Dec. 7, 2016 From the International Searching Authority Re. Application No. PCT/IL2016/050965. (12 Pages).
International Search Report and the Written Opinion dated Dec. 12, 2016 From the International Searching Authority Re. Application No. PCT/IL2016/050966. (10 Pages).
International Search Report and the Written Opinion dated Dec. 12, 2016 From the International Searching Authority Re. Application No. PCT/IL2016/050967. (16 Pages).
International Search Report and the Written Opinion dated Dec. 12, 2016 From the International Searching Authority Re. Application No. PCT/IL2016/050969. (10 Pages).
International Search Report and the Written Opinion dated Oct. 24, 2006 From the International Searching Authority Re. Application No. PCT/IL06/00242.
International Search Report dated Apr. 17, 2006 From the International Searching Authority Re. Application No. PCT/IL04/00490.
Notice of Allowance dated Aug. 6, 2009 From the US Patent and Trademark Office Re. U.S. Appl. No. 11/073,649.
Official Action dated Oct. 11, 2006 From the US Patent and Trademark Office Re. U.S. Appl. No. 11/073,649.
Official Action dated Jun. 28, 2005 From the US Patent and Trademark Office Re. U.S. Appl. No. 11/073,649.
Written Opinion dated Apr. 7, 2006 From the International Searching Authority Re. Application No. PCT/IL04/00490.
Alper et al. "Probing the Specificity of Aminoglycoside—Ribosomal RNA Interactions With Designed Synthetic Analogs", Journal of American Chemical Society, 120: 1965-1978, 1998.
Azimov et al. "G418-Mediated Ribosomal Read-Through of A Nonsense Mutation Causing Autosomal Recessive Proximal Renal Tubular Acidosis", American Journal of Physiology, Renal Physiology, 295(3): F633-F641, Sep. 2008.
Brendel et al. "Readthrough of Nonsense Mutations in Rett Syndrome: Evaluation of Novel Aminoglycosides and Generation of a New Mouse Model", Journal of Molecular Medicine, 89(4): 389-398, Published Online Dec. 1, 2010.
Bryskier "Bacillus Anthracis and Antibacterial Agents", Clinical Microbiology and Infection, 8(8): 467-478, 2002. p. 468, r-h col., Last Line, p. 469, r-h col., Line 3.
Duynstee et al. "An Expeditious Route to the Synthesis of Kelampayosides A and B", Tetrahedron, 55(32): 9881-9898, 1999. Abstract.
Fong et al. "Substrate Promiscuity of an Aminoglycoside Antibiotic Resistance Enzyme Via Target Mimicry", The EMBO Journal, 21(10): 2323-2331, 2002.
Fridman et al "A New Class of Branched Aminoglycosides: Pseudo-Pentasaccharide Derivates of Neomycin B", Organic Letters, 5(20): 3575-3578, 2003. Abstrac, Fig.1, Table 1.
Fridman et al. "Dual Effect of Synthetic Aminoglycosides: Antibacterial Activity Against Bacillus Anthracis and Inhibition of Anthrax Lethal Factor", Angewandte Chemie, International Edition, 44(3): 447-452, 2005.
Goldmann et al. "Beneficial Read-Through of A USH1C Nonsense Mutation by Designed Aminoglycoside NB30 in the Retina", Investigative Ophthalmology & Visual Science, 51(12): 6671-6680, Dec. 2010.
Greenberg et al. "Design and Synthesis of New Aminoglycoside Antibiotics Containing Neamine as an Optimal Core Structure: Correlation of Antibiotic Activity With In Vitro Inhibition of Translation", Journal of American Chemical Society, 121(28): 6527-6541, Jul. 2, 1999.
Haddad et al. "Design of Novel Antibiotics That Bind to the Ribosomal Acyltransfer Site", Journal of American Chemical Society, 124: 3229-3237, 2002.
Haddad et al. "Design of Novel Antibiotics That Bind to the Ribosomal Acyltransfer Site", Journal of the American Chemical Society, JACS, 124(13): 3229-3237, Published Online Mar. 6, 2002.
Hainrichson et al. "Branched Aminoglycosides: Biochemical Studies and Antibacterial Activity of Neomycin B Derivatives", Bioorganic & Medicinal Chemistry, 13(20): 5797-5807, Oct. 15, 2005. p. 5798, r-h col., § 1-6, Fig.1.
Hainrichson et al. "Designer Aminoglycosides: The Race to Develop Improved Antibiotics and Compounds for the Treatment of Human Genetic Diseases", Organic and Biomolecular Chemistry, 6(2): 227-239, Jan. 21, 2008.
Hanessian et al. "Tobramycin Analogues With C-5 Aminoalkyl Ether Chains Intended to Minimize Rings III and IV of Paromomycin", Tetrahedron, 59: 983-993, 2003.
Hobbie et al. "Engineering the rRNA Decoding Site of Eukaryotic Cytosolic Ribosomes in Bacteria", Nucleic Acids Research, 35(18): 6086-6093, Aug. 30, 2007.
Hobbie et al. "Genetic Analysis of Interactions With Eukayotic rRNA Identify the Mitoribosome as Target in Aminoglycoside Ototoxicity", Proc. Natl. Acad. Sci. USA, PNAS, 105(52): 20888-20893, Dec. 30, 2008.
Hobbie et al. "Mitochondrial Deafness Alleles Confer Misreading of the Genetic Code", Proc. Natl. Acad. Sci. USA, PNAS, 105(9): 3244-3249, Mar. 4, 2008.
Kandasamy et al. "Increased Selectivity Toward Cytoplasmic Versus Mitochondrial Ribosome Confers Improved Efficiency of Synthetic Aminoglycosides in Fixing Damaged Genes: A Strategy for Treatment of Genetic Diseases Caused by Nonsense Mutations", Journal of Medicinal Chemistry, 55(23): 10630-10643, Dec. 13, 2012.
Kavadias et al. "Synthesis of a Thioanalogue of Neamine. The Reaction of Nitrosochloroadducts of Glycals With Thiols", Canadian Journal of Chemistry, 57(9): 1056-1063, May 31, 1979. Compound 7b, p. 1059.
Kondo et al. "Differential Selectivity of Natural and Synthetic Aminoglycosides Towards the Eukaryotic and Prokaryotic Decoding a Sites", ChemBioChem, 8(14): 1700-1709, Sep. 24, 2007.
Kotra et al. "Aminoglycosides: Perspectives on Mechanisms of Action and Resistance and Strategies to Counter Resistance", Antimicrobial Agents and Chemotherapy, 44(12): 3249-3256, 2000.
Lee et al. "Inhibition of the Proteolytic Activity of Anthrax Lethal Factor by Aminoglycosides", Journal of the American Chemical Society, 126(15): 4774-4775, 2004.
Lopez-Novoa et al. "New Insights Into the Mechanism of Aminoglycoside Nephrotoxicity: An Integrative Point of View", Kidney International, Online Publication, 79(1): 33-45, Sep. 22, 2010.
Malik et al. "Aminoglycoside-Induced Mutation Suppression (Stop Codon Readthrough) as a Therapeutic Strategy for Duchenne Muscular Dystrophy", Therapeutic Advances in Neurological Disorders, 3(3): 379-389, Nov. 2010.
Mingeot-Leclercq et al. "Aminoglycosides: Activity and Resistance", Antimicrobial Agents and Chemotherapy, 43(4): 727-737, 1999.

(56) References Cited

OTHER PUBLICATIONS

Nudelman "Combined Chemical-Enzymatic Assembly of Aminoglycoside Derivatives With N-1-AHB Side Chain", Advanced Synthesis & Catalysis, 350(11-12): 1682-1688, Published Online Jul. 20, 2008.
Nudelman et al. "Development of Novel Aminoglycoside (NB54) With Reduced Toxicity and Enhanced Suppression of Disease-Causing Premature Stop Mutations", Journal of Medical Chemistry, XP055042341, 52(9): 2836-2845, Mar. 23, 2009.
Nudelman et al. "Redesign of Aminoglycosides for Treatment of Human Genetic Diseases Caused by Premature Stop Mutations", Bioorganic & Medicinal Chemistry Letters, XP002447819, 16(24): 6310-6315, Published Online Sep. 25, 2006.
Nudelman et al. "Repairing Faulty Genes by Aminoglycosides: Development of New Derivatives of Geneticin (G418) With Enhanced Suppression of Diseases-Causing Nonsense Mutations", Bioorganic and Medicinal Chemistry, XP055017979, 18(11): 3735-3746, Jun. 1, 2010. Abstract, Introduction, p. 3735, Compounds 7, 8, Fig.1, p. 3736, Compounds 5, 6, 7, 8.
Rebibo-Sabbah et al. "In Vitro and Ex Vivo Suppressing by Aminoglycosides of PCDH15 Nonsense Mutations Underlying Type 1 Usher Syndrome", Human Genetics, 122(3-4): 373-381, Published Online Jul. 25, 2007.
Rowe et al. "Suppression of CFTR Premature Termination Codons and Rescue of CFTR Protein and Function by the Synthetic Aminoglycoside NB54", Journal of Molecular Medicine, 89(11): 1149-61, Jul. 2011.
Sabbavarapu et al. "Design of Novel Aminoglycoside Derivatives With Enhanced Suppression of Diseases-Causing Nonsense Mutations", ACS Medical Chemistry Letters, 7(4): 418-423, Feb. 11, 2016.
Shalev et al. "Identification of the Molecular Attributes Required for Aminoglycoside Activity Against Leishmania", Proc. Natl. Acad. Sci. USA, PNAS, 110(33): 13333-13338, Aug. 13, 2013.
Shalev et al. "Structural Basis for Selective Targeting of Leishmanial Ribosomes: Aminoglycoside Derivatives as Promising Therapeutics", Nucleic Acids Research, 43(17): 8601-8613, Published Online Aug. 11, 2015.
Shalev et al. "Towards Catalytic Antibiotics", Schulich Faculty of Chemistry, Technion, Haifa, Israel, Poster, 2013.
Shulman et al. "Designer Aminoglycosides That Selectively Inihibit Cytoplasmic Rather Than Mitochondrial Ribosomes Show Decreased Ototoxicity. A Strategy for the Treatment of Genetic Diseases", the Journal of Biological Chemistry, 289(4): 2318-2330, Published Online Dec. 3, 2013.
Simonsen et al. "Novel Paromamine Derivatives Exploring Shallow-Groove Recognition of Ribosomal-Decoding-Site RNA", ChemBioChem, 3(12): 1223-1228, Dec. 31, 2002. Compounds 14, 16, Cheme 2, p. 1225.
Smolkin et al. "Towards Catalytic Antibiotics", Schulich Faculty of Chemistry, Technion, Haifa, Israel, Poster, 2014.
Smolkin et al. "Towards Catalytic Antibiotics", Schulich Faculty of Chemistry, Technion, Haifa, Israel, Poster, 2015.
Umezawa et al. "The Total Synthesis of Neomycin C", Bulletin of the Chemical Society of Japan, 53(11): 3259-3262, Nov. 1980. Compound 3, 6, 3',4',5'-Tetra-0-Acetyl-1,3,2',6'-Tetra-N-(Benzyloxycarbonyl)Ribostamycin, p. 3259.
Vecsler et al. "Ex Vivo Treatment With a Novel Synthetic Aminoglycoside NB54 in Primary Fibroblasts From Rett Syndrome Patients Suppresses MECP2 Nonsense Mutations", PLoS ONE, XP055209360, 6(6): e20733-1-e20733-8, Jun. 13, 2011.
Venkataraman et al. "Reawakening Retrocyclins: Ancestral Human Defensins Active Against HIV-1", PLoS Biology, 7(4): e1000095-0720-e1000095-0729, Apr. 2009.
Wang et al. "A Hybrid Drug Limits Resistance by Evading the Action of the Multiple Antibiotic Resistance Pathway", Molecular Biology and Evolution, 33(2): 492-500, Advance Access Publication Nov. 3, 2015.
Wang et al. "The Synthesis of L-Aminosugar and the Studies of L-Pyranoses on the Ring III of Pyranmycins", Organic Letters, 4(23): 3997-4000, 2002.
Warchol "Cellular Mechanisms of Aminoglycoside of Aminoglycoside Ototoxicity", Current Opinion in Otolaryngology & Head and Neck Surgery, 18(5): 454-458, Oct. 2010.
Supplementary European Search Report and the European Search Opinion dated Apr. 1, 2019 From the European Patent Office Re. Application No. 16840986.0. (6 Pages).
Supplementary European Search Report and the European Search Opinion dated Mar. 27, 2019 From the European Patent Office Re. Application No. 16840987.8. (10 Pages).
EPO, Extended European Search Report for European Application No. 16840988.6, dated Aug. 21, 2019. 8 pages.
EPO, Extended European Search Report for European Application No. 16883508.0, dated Sep. 12, 2019. 10 pages.
USPTO, Restriction Requirement for U.S. Appl. No. 16/068,165, dated Aug. 9, 2019. 7 pages.
USPTO, Restriction Requirement for U.S. Appl. No. 15/756,691, dated Aug. 9, 2019. 7 pages.
USPTO, Restriction Requirement for U.S. Appl. No. 15/756,665, dated Aug. 9, 2019. 7 pages.
Davies, D.H. et al. "Semisynthetic aminoglycoside antibacterials. 6. Synthesis of sisomicin, antibiotic G-52, and novel 6'-substituted analogs of sisomicin from aminoglycoside 66-40C" Journal of Medicinal Chemistry (Feb. 1978), pp. 189-193.
Maianti, J. et al. Structural hybridization of three aminoglycoside antibiotics yields a potent broad-spectrum bactericide that eludes bacterial resistance enzymes: Med Chem Comm (Jan. 2016) vol. 7, No. 1, pp. 170-176.
IPA, First Examination Report for Australian Patent Application No. 2016314379. dated Mar. 25, 2020. 4 pages.
IPI, First Examination Report for Indian Patent Application No. 201827011427. dated Feb. 25, 2020. 7 pages.
IPO, Office Action for Israeli Patent Application No. 257820. dated Feb. 23, 2020. 9 pages with English translation.
JPO, Notice of Reasons for Rejection for Japanese Patent Application No. 2018-511473. dated May 26, 2020. 15 pages with English translation.
USPTO, Non-Final Office Action for U.S. Appl. No. 15/756,665. dated Jan. 27, 2020. 12 pages.
USPTO, Restriction Requirement for U.S. Appl. No. 15/756,691. dated Jan. 24, 2020. 5 pages.
USPTO, Non-Final Office Action for U.S. Appl. No. 15/756,691. dated Jun. 26, 2020. 11 pages.
Nudelman, I. et al. "Repairing faulty genes by aminoglycosides: Development of new derivatives of geneticin (G418) with enhanced suppression of diseases-causing nonsense mutations" Bioorganic & Medicinal Chemistry, 2010, vol. 18, p. 3735-3746.
Registry [online], Dec. 9, 2011, [Searched on Apr. 28, 2020], Retrieved from: STN, CAS Registration No. 1350556-52-3.
Registry [online], Nov. 16, 1984, [Searched on Apr. 28, 2020], Retrieved from: STN, CAS Registration No. 79504-04-4.
Registry [online], Dec. 9, 2011, [Searched on Apr. 28, 2020], Retrieved from: STN, CAS Registration No. 1350556-51-2.

Compound A1

Compound A2

Compound B1

Compound B2

Compound C1

Compound C2

FIG. 2 - Continued
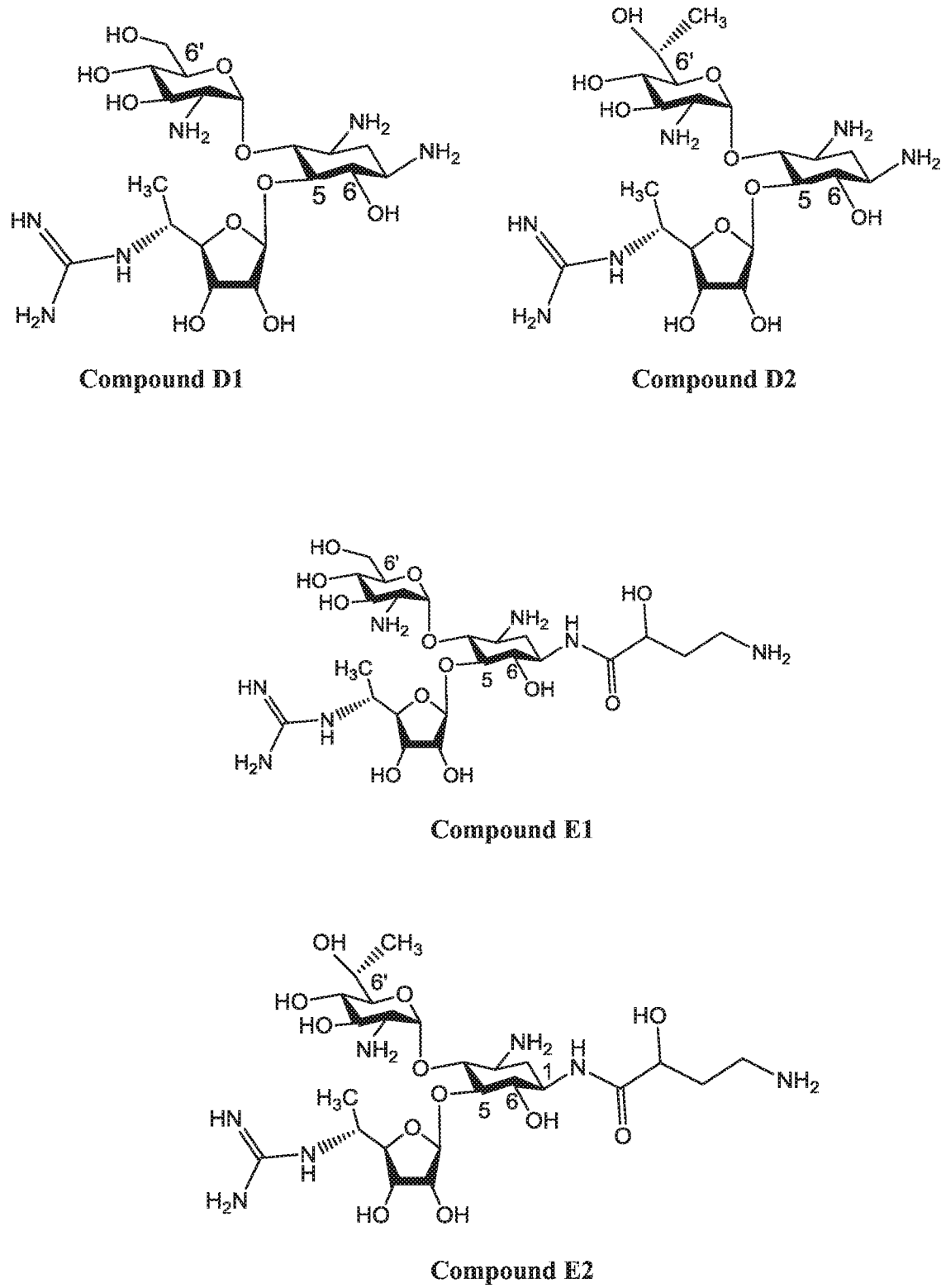
Compound D1
Compound D2
Compound E1
Compound E2

AMINOGLYCOSIDE DERIVATIVES AND USES THEREOF IN TREATING GENETIC DISORDERS

RELATED APPLICATIONS

This application is a National Phase of PCT Patent Application No. PCT/IL2016/050966 having International filing date of Sep. 2, 2016, which claims the benefit of priority under 35 USC § 119(e) of U.S. Provisional Patent Application No. 62/213,187 filed on Sep. 2, 2015. The contents of the above applications are all incorporated by reference as if fully set forth herein in their entirety.

FIELD AND BACKGROUND OF THE INVENTION

The present invention, in some embodiments thereof, relates to a new class of aminoglycosides and more particularly, but not exclusively, to novel aminoglycoside derivatives and their use in increasing an expression of a gene having a stop codon mutation and/or in the treatment of genetic disorders (e.g., genetic disorders associated with a stop codon mutation).

Many human genetic disorders result from nonsense mutations, where one of the three stop codons (UAA, UAG or UGA) replaces an amino acid-coding codon, leading to premature termination of the translation and eventually to truncated inactive proteins. Currently, hundreds of such nonsense mutations are known, and several were shown to account for certain cases of fatal diseases, including, for example, cystic fibrosis (CF), Duchenne muscular dystrophy (DMD), ataxia-telangiectasia, Hurler syndrome, hemophilia A, hemophilia B, Tay-Sachs disease, and more. For many of those diseases there is presently no effective treatment.

Some aminoglycoside compounds have been shown to have therapeutic value in the treatment of several genetic diseases because of their ability to induce ribosomes to read-through stop codon mutations, generating full-length proteins from part of the mRNA molecules.

Aminoglycosides are highly potent, broad-spectrum antibiotics commonly used for the treatment of life-threatening infections. It is accepted that the mechanism of action of aminoglycoside antibiotics, such as paromomycin (see, FIG. 1), involves interaction with the prokaryotic ribosome, and, more specifically, involves binding to the decoding A-site of the 16S ribosomal RNA, which leads to protein translation inhibition and interference with the translational fidelity.

Several achievements in bacterial ribosome structure determination, along with crystal and NMR structures of bacterial A-site oligonucleotide models, have provided useful information for understanding the decoding mechanism in prokaryote cells and understanding how aminoglycosides exert their deleterious misreading of the genetic code. These studies and others have given rise to the hypothesis that the affinity of the A-site for a non-cognate mRNA-tRNA complex is increased upon aminoglycoside binding, preventing the ribosome from efficiently discriminating between non-cognate and cognate complexes.

The enhancement of termination suppression by aminoglycosides in eukaryotes is thought to occur in a similar mechanism to the aminoglycosides' activity in prokaryotes of interfering with translational fidelity during protein synthesis, namely the binding of certain aminoglycosides to the ribosomal A-site probably induce conformational changes that stabilize near-cognate mRNA-tRNA complexes, instead of inserting the release factor. Aminoglycosides have been shown to suppress various stop codons with notably different efficiencies (UGA>UAG>UAA), and the suppression effectiveness has been found to be further dependent upon the identity of the fourth nucleotide immediately downstream from the stop codon (C>U>A≥grams) as well as the local sequence context around the stop codon.

The desired characteristics of an effective read-through drug would be oral administration and little or no effect on bacteria. Antimicrobial activity of read-through drug is undesirable as any unnecessary use of antibiotics, particularly with respect to the gastrointestinal (GI) biota, due to the adverse effects caused by upsetting the GI biota equilibrium and the emergence of resistance. In this respect, in addition to the abovementioned limitations, the majority of clinical aminoglycosides are greatly selective against bacterial ribosomes, and do not exert a significant effect on cytoplasmic ribosomes of human cells.

In an effort to circumvent the abovementioned limitations, the biopharmaceutical industry is seeking new stop codon mutations suppression drugs by screening large chemical libraries for nonsense read-through activity.

The first experiments of aminoglycoside-mediated suppression of cystic fibrosis transmembrane conductance regulator protein (CFTR) stop codon mutations demonstrated that premature stop codon mutations found in the CFTR gene could be suppressed by members of the gentamicin family and Geniticin® (G-418), as measured by the appearance of full-length, functional CFTR in bronchial epithelial cell lines.

Suppression experiments of intestinal tissues from CFTR−/− transgenic mice mutants carrying a human CFTR-G542X transgene showed that treatment with gentamicin, and to lesser extent tobramycin, have resulted in the appearance of human CFTR protein at the glands of treated mice. Most importantly, clinical studies using double-blind, placebo-controlled, crossover trails have shown that gentamicin can suppress stop codon mutations in affected patients, and that gentamicin treatment improved transmembrane conductance across the nasal mucosa in a group of 19 patients carrying CFTR stop codon mutations. Other genetic disorders for which the therapeutic potential of aminoglycosides was tested in in-vitro systems, cultured cell lines, or animal models include DMD, Hurler syndrome, nephrogenic diabetes insipidus, nephropathic cystinosis, retinitis pigmentosa, and ataxia-telangiectasia.

However, one of the major limitations in using aminoglycosides as pharmaceuticals is their high toxicity towards mammals, typically expressed in kidney (nephrotoxicity) and ear-associated (ototoxicity) illnesses. The origin of this toxicity is assumed to result from a combination of different factors and mechanisms such as interactions with phospholipids, inhibition of phospholipases and the formation of free radicals. Although considered selective to bacterial ribosomes, most aminoglycosides bind also to the eukaryotic A-site but with lower affinities than to the bacterial A-site. The inhibition of translation in mammalian cells is also one of the possible causes for the high toxicity of these agents. Another factor adding to their cytotoxicity is their binding to the mitochondrial ribosome at the 12S rRNA A-site, whose sequence is very close to the bacterial A-site.

Many studies have been attempted to understand and offer ways to alleviate the toxicity associated with aminoglycosides, including the use of antioxidants to reduce free radical levels, as well as the use of poly-L-aspartate and daptomycin, to reduce the ability of aminoglycosides to interact with phospholipids. The role of megalin (a multiligand endocytic receptor which is especially abundant in the kidney proximal tubules and the inner ear) in the uptake of aminoglycosides has recently been demonstrated. The administration of agonists that compete for aminoglycoside binding to megalin also resulted in a reduction in aminoglycoside uptake and toxicity. In addition, altering the administration schedule and/or the manner in which aminoglycosides are administered has been investigated as means to reduce toxicity.

Despite extensive efforts to reduce aminoglycoside toxicity, few results have matured into standard clinical practices and procedures for the administration of aminoglycosides to suppress stop codon mutations, other than changes in the administration schedule. For example, the use of sub-toxic doses of gentamicin in the clinical trials probably caused the reduced read-through efficiency obtained in the in-vivo experiments compared to the in-vitro systems. The aminoglycoside Geneticin® (also known as G-418 sulfate or simply G-418) showed the best termination suppression activity in in-vitro translation-transcription systems, however, its use as a therapeutic agent is not possible since it is lethal even at very low concentrations. For example, the $LD_{50}$ of G-418 against human fibroblast cells is 0.04 mg/ml, compared to 2.5-5.0 mg/ml for gentamicin, neomycin and kanamycin.

The increased sensitivity of eukaryotic ribosomes to some aminoglycoside drugs, such as G-418 and gentamicin, is intriguing but up to date could not be rationally explained because of the lack of sufficient structural data on their interaction with eukaryotic ribosomes. Since G-418 is extremely toxic even at very low concentrations, presently gentamicin is the only aminoglycoside tested in various animal models and clinical trials. Although some studies have shown that due to their relatively lower toxicity in cultured cells, amikacin and paromomycin can represent alternatives to gentamicin for stop codon mutation suppression therapy, no clinical trials with these aminoglycosides have been reported yet.

To date, nearly all suppression experiments have been performed with clinical, commercially available aminoglycosides, however, only a limited number of aminoglycosides, including gentamicin, amikacin, and tobramycin, are in clinical use as antibiotics for internal administration in humans. Among these, tobramycin do not have stop codon mutations suppression activity, and gentamicin is the only aminoglycoside tested for stop codon mutations suppression activity in animal models and clinical trials. Recently, a set of neamine derivatives were shown to promote read-through of the SMN protein in fibroblasts derived from spinal muscular atrophy (SPA) patients; however, these compounds were originally designed as antibiotics and no conclusions were derived for further improvement of the read-through activity of these derivatives.

WO 2007/113841, which is incorporated by reference as if fully set forth herein, teaches a class of paromomycin-derived aminoglycosides, which were designed specifically to exhibit high premature stop codon mutations readthrough activity while exerting low cytotoxicity in mammalian cells and low antimicrobial activity, and can thus be used in the treatment of genetic diseases. This class of paromomycin-derived aminoglycosides was designed by introducing certain manipulations of a paromamine core, which lead to enhanced readthrough activity and reduced toxicity and antimicrobial activity. The manipulations were made on several positions of the paromamine core.

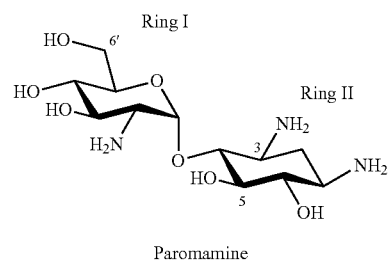

Paromamine

One such manipulation of the paromamine core which has been described in WO 2007/113841 is the determination of the beneficial role of a hydroxyl group at position 6' of the aminoglycoside core (see, for example, NB30 and NB54 below).

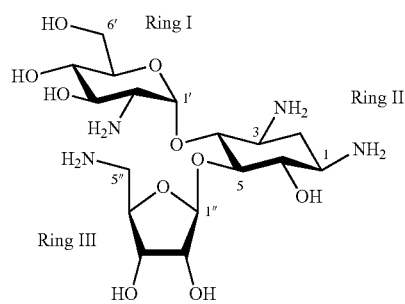

NB30

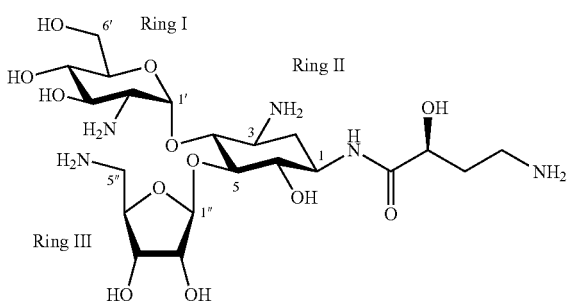

NB54

Another manipulation of the paromamine core which has been defined and demonstrated in WO 2007/113841 is the introduction of one or more monosaccharide moieties or an oligosaccharide moiety at position 3', 5 and/or 6 of the aminoglycoside core. This manipulation is reflected as "Ring III" in the exemplary compounds NB30 and NB54 shown hereinabove.

An additional manipulation of the paromamine core which has been defined and demonstrated in WO 2007/113841 is the introduction of an (S)-4-amino-2-hydroxybutyryl (AHB) moiety at position 1 of the paromamine core. This manipulation is reflected in exemplary compound NB54 shown hereinabove. It has been demonstrated that such an introduction of an AHB moiety provides for enhanced readthrough activity and reduced toxicity.

An additional manipulation of the paromamine core which has been described in WO 2007/113841 is the substitution of hydrogen at position 6' by an alkyl such as a methyl substituent. This manipulation has been exemplified in derivatives of compounds NB30 and NB54, referred to as NB74 and NB84 respectively.

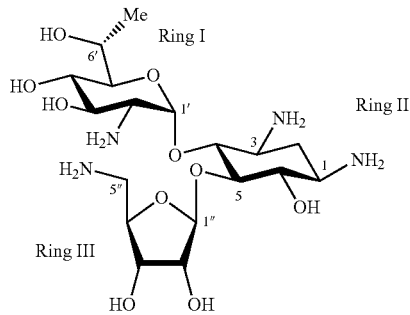

NB74

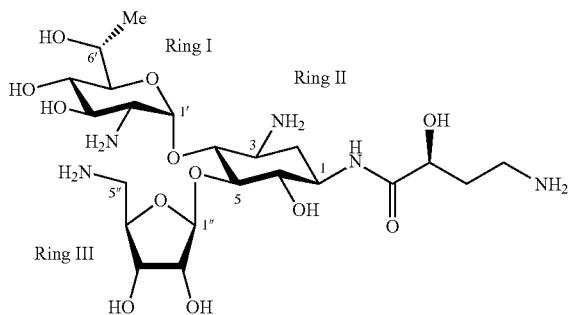

NB84

WO 2012/066546, which is incorporated by reference as if fully set forth herein, discloses another class of pseudo-trisaccharide aminoglycosides, which exhibit efficient stop codon mutation readthrough activity, low cytotoxicity and high selectivity towards eukaryotic translation systems. These pseudo-trisaccharide aminoglycosides feature an alkyl group at the 5" position, reflected in exemplary compounds NB122 and NB124.

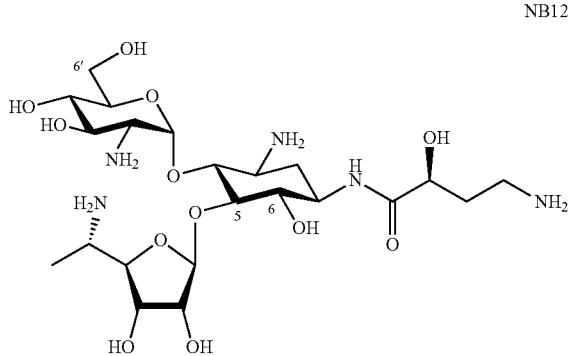

NB122

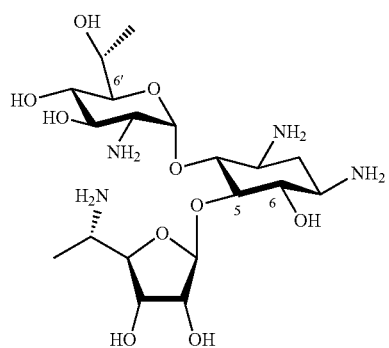

NB124

Additional background art includes Nudelman, I., et al., Bioorg Med Chem Lett, 2006. 16(24): p. 6310-5; Hobbie, S. N., et al., Nucleic Acids Res, 2007. 35(18): p. 6086-93; Kondo, J., et al., Chembiochem, 2007. 8(14): p. 1700-9; Rebibo-Sabbah, A., et al., Hum Genet, 2007. 122(3-4): p. 373-81; Azimov, R., et al., Am J Physiol Renal Physiol, 2008. 295(3): p. F633-41; Hainrichson, M., et al., Org Biomol Chem, 2008. 6(2): p. 227-39; Hobbie, S. N., et al., Proc Natl Acad Sci USA, 2008. 105(52): p. 20888-93; Hobbie, S. N., et al., Proc Natl Acad Sci USA, 2008. 105(9): p. 3244-9; Nudelman, I., et al., Adv. Synth. Catal., 2008. 350: p. 1682-1688; Nudelman, I., et al., J Med Chem, 2009. 52(9): p. 2836-45; Venkataraman, N., et al., PLoS Biol, 2009. 7(4): p. e95; Brendel, C., et al., J Mol Med (Berl), 2010. 89(4): p. 389-98; Goldmann, T., et al., Invest Ophthalmol Vis Sci, 2010. 51(12): p. 6671-80; Malik, V., et al., Ther Adv Neurol Disord, 2010. 3(6): p. 379-89; Nudelman, I., et al., Bioorg Med Chem, 2010. 18(11): p. 3735-46; Warchol, M. E., Curr Opin Otolaryngol Head Neck Surg, 2010. 18(5): p. 454-8; Lopez-Novoa, J. M., et al., Kidney Int, 2011. 79(1): p. 33-45; Rowe, S. M., et al., J Mol Med (Berl), 2011. 89(11): p. 1149-61; Vecsler, M., et al., PLoS One, 2011. 6(6): p. e20733; U.S. Pat. Nos. 3,897,412, 4,024,332, 4,029,882, and 3,996,205; Greenberg et al., J. Am. Chem. Soc. 1999, 121, 6527-6541; Kotra et al., antimicrobial agents and chemotherapy, December 2000, p. 3249-3256; Haddad et al., J. Am. Chem. Soc. 2002, 124, 3229-3237; and FR Patent No. 2,427,341, JP Patent No. 04046189. The teachings of all of these documents are incorporated by reference as if fully set forth herein.

SUMMARY OF THE INVENTION

The present invention relates to a new class of pseudo-trisaccharide aminoglycosides, which can be beneficially used in the treatment of genetic diseases, by exhibiting high premature stop codon mutations read-through activity, low toxicity in mammalian cells and low antimicrobial activity, as well as improved bioavailability and/or cell permeability. The presently disclosed aminoglycosides are characterized by a core structure based on Rings I and II of paromomycin, and include an additional ring, Ring III.

According to an aspect of some embodiments of the present invention there is provided a compound represented by general Formula I:

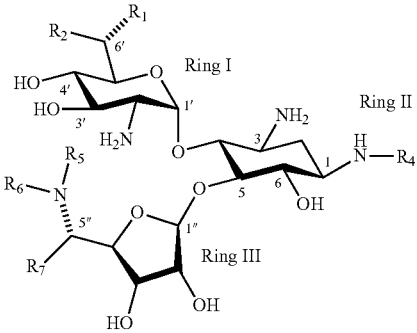

Formula I or a pharmaceutically acceptable salt thereof, wherein:

the dashed lines indicate a stereo-configuration of position 6' being an R configuration or an S configuration;

$R_1$ is selected from hydrogen, alkyl, cycloalkyl or aryl;

$R_2$ is selected from a substituted or unsubstituted alkyl, OR' and NR'R", wherein each of R' and R" is independently selected from hydrogen, a substituted or unsubstituted alkyl, a substituted or unsubstituted cycloalkyl, a substituted or unsubstituted aryl, a substituted or unsubstituted heteroaryl, a substituted or unsubstituted alkaryl, and an acyl;

$R_4$ is selected from hydrogen, acyl, an amino-substituted alpha-hydroxy acyl, a substituted or unsubstituted alkyl, a substituted or unsubstituted cycloalkyl, a substituted or unsubstituted aryl, a substituted or unsubstituted alkaryl, and a cell-permealizable group;

$R_5$ and $R_6$ are each independently selected from hydrogen, a substituted or unsubstituted alkyl, a substituted or unsubstituted cycloalkyl, a substituted or unsubstituted aryl, a substituted or unsubstituted alkaryl, a substituted or unsubstituted heteroaryl, acyl, and a cell-permealizable group, or, alternatively, $R_5$ and $R_6$ form together a heterocyclic ring; and $R_7$ is alkyl, cycloalkyl or aryl, provided that:

when $R_2$ is hydroxy, $R_4$ is not hydrogen, AHB or AHP, and/or at least one of $R_5$ and/or $R_6$, if present, is not hydrogen.

According to some of any of the embodiments of the present invention, $R_7$ is alkyl.

According to some of any of the embodiments of the present invention, $R_7$ is methyl.

According to some of any of the embodiments of the present invention, $R_1$ is alkyl, e.g., methyl.

According to some of any of the embodiments of the present invention, $R_1$ is a non-substituted alkyl.

According to some of any of the embodiments of the present invention, $R_1$ is hydrogen.

According to some of any of the embodiments of the present invention, $R_2$ is OR'.

According to some of any of the embodiments of the present invention, R' is hydrogen.

According to some of any of the embodiments of the present invention, $R_4$ is selected from hydrogen, a substituted or unsubstituted alkyl, a substituted or unsubstituted cycloalkyl, a substituted or unsubstituted alkaryl, a substituted or unsubstituted acyl and an amino-substituted alpha-hydroxy acyl.

According to some of any of the embodiments of the present invention, $R_4$ is a substituted or unsubstituted alkyl.

According to some of any of the embodiments of the present invention, $R_5$ and $R_6$ are each hydrogen.

According to some of any of the embodiments of the present invention, one of $R_5$ and $R_6$ is a cell-permealizable group.

According to some of any of the embodiments of the present invention, the cell-permealizable group is selected from guanidinyl and guanyl.

According to some of any of the embodiments of the present invention, one of $R_5$ and $R_6$ is a guanidinyl.

According to an aspect of some embodiments of the present invention, there is provided a pharmaceutical composition comprising the compound as described herein and a pharmaceutically acceptable carrier.

According to some embodiments of the present invention, the pharmaceutical composition is packaged in a packaging material and identified in print, in or on the packaging material, for use in the treatment of a genetic disorder.

According to an aspect of some embodiments of the present invention, there is provided a method of treating a genetic disorder, the method comprising administering to a subject in need thereof a therapeutically effective amount of the compound as described herein.

According to an aspect of some embodiments of the present invention, there is provided a compound as described herein in any of the respective embodiments and any combination thereof, for use in the treatment of a genetic disorder.

According to an aspect of some embodiments of the present invention, there is provided a use of the compound as described herein in any of the respective embodiments and any combination thereof in the manufacture of a medicament for treating a genetic disorder.

According to some of any of the embodiments described herein, the genetic disorder is associated with a premature stop codon mutation and/or a protein truncation phenotype.

According to some of any of the embodiments described herein, the genetic disorder is selected from the group consisting of cystic fibrosis (CF), Duchenne muscular dystrophy (DMD), ataxia-telangiectasia, Hurler syndrome, hemophilia A, hemophilia B, Usher syndrome, Tay-Sachs disease, Becker muscular dystrophy (BMD), Congenital muscular dystrophy (CMD), Factor VII deficiency, Familial atrial fibrillation, Hailey-Hailey disease, McArdle disease, Mucopolysaccharidosis, Nephropathic cystinosis, Polycystic kidney disease, Rett syndrome, Spinal muscular atrophy (SMA), X-linked nephrogenic diabetes insipidus (XNDI) and X-linked retinitis pigmentosa.

According to an aspect of some embodiments of the present invention there is provided a method of increasing the expression level of a gene having a premature stop-codon mutation, the method comprising translating the gene into a protein in the presence of a compound as described herein in any of the respective embodiments and any combination thereof.

According to an aspect of some embodiments of the present invention there is provided a compound as described herein in any of the respective embodiments and any combination thereof for use in increasing the expression level of a gene having a premature stop-codon mutation.

According to an aspect of some embodiments of the present invention there is provided a use of a compound as described herein in any of the respective embodiments and any combination thereof in the manufacture of a medicament for increasing the expression level of a gene having a premature stop-codon mutation.

According to some of any of the embodiments described herein, the premature stop-codon mutation has an RNA code selected from the group consisting of UGA, UAG and UAA.

According to some of any of the embodiments described herein, the protein is translated in a cytoplasmic translation system.

According to some of any of the embodiments described herein, the compound is used in a mutation suppression amount.

According to some of any of the embodiments described herein, an inhibition of translation $IC_{50}$ of the compound in a eukaryotic cytoplasmic translation system is greater that an inhibition of translation $IC_{50}$ of the compound in a ribosomal translation system.

According to some of any of the embodiments described herein, an inhibition of translation $IC_{50}$ of the compound in a eukaryotic cytoplasmic translation system is greater that an inhibition of translation $IC_{50}$ of the compound in a prokaryotic translation system.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
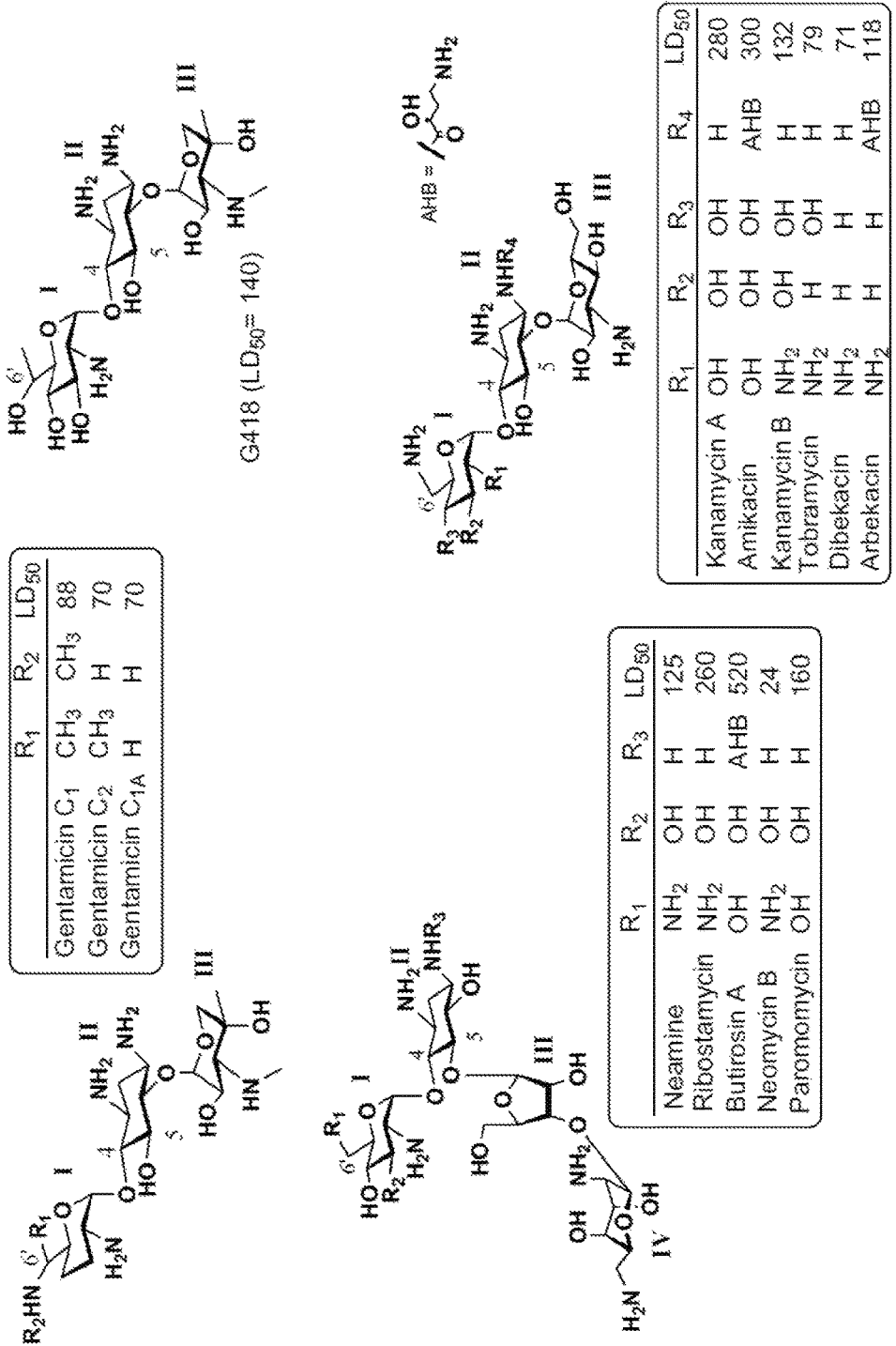
FIG. 1 (Background Art) presents the chemical structures of some known families of aminoglycosides.

The present invention, in some embodiments thereof, relates to a new class of aminoglycosides and more particularly, but not exclusively, to novel aminoglycoside derivatives and their use in increasing an expression of a gene having a stop codon mutation and/or in the treatment of genetic disorders (e.g., genetic disorders associated with a stop codon mutation).

Specifically, the present invention, in some embodiments thereof, relates to a novel aminoglycoside compounds, derived from paromomycin, which exhibit high premature stop codon mutations readthrough activity while exerting low toxicity in mammalian cells, and which are characterized by improved bioavailability and/or cell permeability. Embodiments of the present invention are further of pharmaceutical compositions containing these compounds, and of uses thereof in increasing an expression level of a gene having a stop codon mutation and/or in inducing and/or promoting readthrough a stop codon mutation and/or in the treatment of genetic disorders. Embodiments of the present invention are further of processes of preparing these compounds.

The principles and operation of the present invention may be better understood with reference to the figures and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed hereinabove, the use aminoglycosides as therapeutic agents is limited primarily due to their high toxicity. In the context of treatment of genetic disorders, such a use is further limited by the antibacterial activity exhibited by the aminoglycosides, which can also translate into toxicity.

Additional limitations associated with aminoglycosides include low bioavailability, which typically requires an intravenous or subcutaneous administration, and poor permeability into eukaryotic cells, which typically requires administration of high doses which are associated with adverse side effected. It is assumed that the high water solubility and polarity of aminoglycosides limits their absorbance through intestinal tissues and their permeability through cell membranes.

As further discussed hereinabove, several structural manipulations on the structure of paromamine have given rise to synthetic aminoglycosides which have been shown to exert improved premature stop codon mutations readthrough activity while exerting low toxicity in mammalian cells. WO 2007/113841 and WO 2012/066546, which are incorporated by reference as if fully set forth herein, describe such aminoglycosides, and scheme 1 below presents the structural manipulations of the paromamine structure disclosed therein:

Scheme 1 (Background Art)

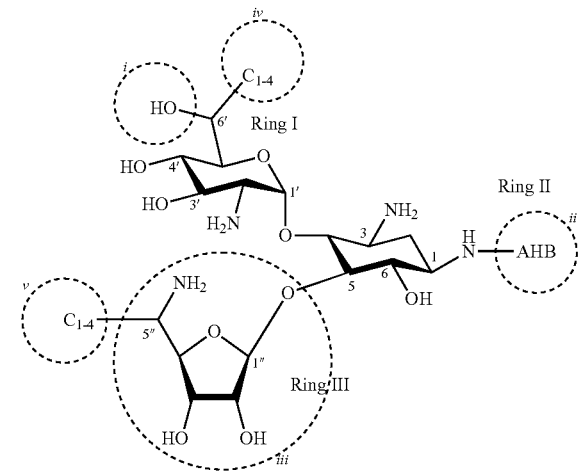

wherein "i" refers to the provision of a hydroxyl group in position 6'; "ii" refers to the provision of an AHB group in position N1; "iii" refers to the provision of a third saccharide moiety (Ring III) attached to the second saccharide ring; "iv" is the provision of a modification at position 6' (exemplified in Scheme 1 as a lower alkyl); and "v" refers to the provision of modification at position 5" (exemplified in Scheme 1 as a lower alkyl).

While further deciphering the structure-activity relationship of such aminoglycosides, in an attempt to further improve their therapeutic effect in the context of genetic disorders, the present inventor has now designed numerous additional modifications, at varying positions of the paromamine structure, which are collectively represented herein by Formula I.

These compounds represent a new generation of paromamine-derived aminoglycosides which overcome limitations associated with administration of aminoglycosides, as discussed supra.

While reducing the present invention to practice, the present inventor has designed exemplary novel aminoglycosides structures, collectively represented by Formula I herein, which feature at least some of the structural modifications presented in Scheme 1 above, and which feature further manipulations, for example, at points "ii" and "iii" depicted in Scheme 1, involving introduction of hydrophobic moieties and/or positively-charged, cell-permealizable moieties at these points.

The Compounds:

According to an aspect of some embodiments of the present invention, there are provided novel aminoglycoside compounds (also referred to herein as "aminoglycoside derivatives", which are pseudo-trisaccharides collectively represented by Formula I:

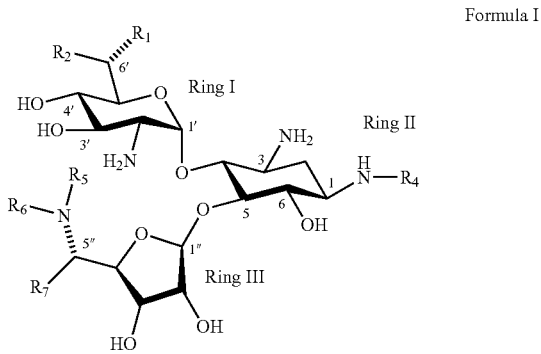

or a pharmaceutically acceptable salt thereof,
wherein:
the dashed lines independently indicates a stereo-configuration of position 6' and/or 5" being an R configuration or an S configuration;

$R_1$ is selected from hydrogen, alkyl, cycloalkyl or aryl;

$R_2$ is selected from a substituted or unsubstituted alkyl, OR' and NR'R", wherein each of R' and R" is independently selected from hydrogen, a substituted or unsubstituted alkyl, a substituted or unsubstituted cycloalkyl, a substituted or unsubstituted aryl, a substituted or unsubstituted heteroaryl, a substituted or unsubstituted alkaryl, and an acyl;

$R_4$ is selected from hydrogen, acyl, an amino-substituted alpha-hydroxy acyl, a substituted or unsubstituted alkyl, a substituted or unsubstituted cycloalkyl, a substituted or unsubstituted aryl, a substituted or unsubstituted alkaryl, and a cell-permealizable group, as described herein;

$R_5$ and $R_6$ are each independently selected from hydrogen, a substituted or unsubstituted alkyl, a substituted or unsubstituted cycloalkyl, a substituted or unsubstituted aryl, a substituted or unsubstituted alkaryl, a substituted or unsubstituted heteroaryl, acyl, and a cell-permealizable group, as described herein, or, alternatively, $R_5$ and $R_6$ form together a heterocyclic ring; and $R_7$ is alkyl, cycloalkyl or aryl.

According to some embodiments of the present invention, excluded from the scope of the present invention are compounds known in the art, including any of the documents cited in the Background section of the instant application, which are encompassed by Formula I. Exemplary compounds which are excluded from the scope of the present embodiments include, but are not limited to, compounds represented by Formula I, in which $R_2$ is hydroxy, $R_4$ is hydrogen, AHB or AHP, or equivalents of AHB and AHP, as defined in WO 2007/113841 and WO 2012/066546, and $R_5$ and $R_6$ are each hydrogen.

According to some embodiments of the present invention, when $R_2$ is hydroxy, then $R_4$ is not hydrogen, AHB or AHP, or equivalents of AHB and AHP, as defined in WO 2007/113841 and WO 2012/066546, and/or one or both of $R_5$ and $R_6$, if present, is not hydrogen.

According to some embodiments of the present invention, one or both of the amine substituents at positions 1 or 5" of the aminoglycoside structure is modified, such that $R_4$ and/or one or both of $R_5$ and $R_6$ is not hydrogen.

Herein throughout, an amine which bears a substituent other than hydrogen is referred to herein as a "modified amine substituent" or simply as a "modified amine".

According to some embodiments of the present invention, one or both of the amine substituents at positions 1 or 5" of the aminoglycoside structure is modified to include a hydrophobic moiety such as alkyl, cycloalkyl, alkaryl and/or aryl, or a group which is positively-charged at physiological pH and which can increase cell permeability of the compound (also referred to herein interchangeably as "cell-permealizable group" or "cell-permealizing group"), such as guanine or guanidine groups, as defined herein, or, alternatively, hydrazine, hidrazide, thiohydrazide, urea and thiourea.

In some of any of the embodiments described herein, $R_1$ is alkyl, and in some embodiments it is a lower alkyl, of 1 to 4 carbon atoms, including, but not limited to, methyl, ethyl, propyl, butyl, isopropyl, and isobutyl.

In some of any of the embodiments described herein, $R_1$ is a non-substituted (unsubstituted) alkyl.

In some of any of the embodiments described herein, $R_1$ is methyl.

Alternatively, in some of any of the embodiments described herein, $R_1$ is cycloalkyl, including, but not limited to, cyclopropyl, cyclobutyl, cyclopentyl and cyclohexyl.

Further alternatively, in some of any of the embodiments described herein, $R_1$ is aryl, such as a substituted or unsubstituted phenyl. Non-limiting examples include unsubstituted phenyl and toluene.

Further alternatively, in some of any of the embodiments described herein, $R_1$ is alkaryl, such as a substituted or unsubstituted benzyl.

In some of any of the embodiments described herein, $R_1$ and $R_7$ are each independently selected from alkyl, aryl and cycloalkyl, as described herein, and in some embodiments, $R_1$ and $R_7$ are each independently an alkyl. In some embodiments, $R_1$ and $R_7$ are each methyl.

In some of any of the embodiments described herein $R_2$ is OR'.

In some of these embodiments, R' is hydrogen, and $R_2$ is hydroxy.

In other embodiments, $R_2$ is OR' and R' is other than hydrogen.

In some of these embodiments, R' is a substituted or unsubstituted alkyl, as defined herein, or a substituted or unsubstituted cycloalkyl, as defined herein, and $R_2$ is alkoxy.

In some of these embodiments, R' is a substituted or unsubstituted aryl, as defined herein, and $R_2$ is aryloxy.

In some of these embodiments, R' is acyl, as defined herein, and $R_2$ is carboxylate, as defined herein.

Alternatively, $R_2$ is NR'R".

In some of these embodiments, R' and R" are both hydrogen.

In some of these embodiments, one or both of R' and R" is other than hydrogen.

Exemplary chemical groups which can be represented by variable $R_2$ in Formula I, when $R_2$ is NR'R", include, but are not limited to, compounds in which R' is hydrogen and R" is alkyl amino, such as NH—$(CH_2)$n-$NH_2$, with n being, for example, from 1 to 6; compounds in which R' is hydrogen and R" is NH—$(CH_2)$n-OH, with n being, for example, from 1 to 6; compounds in which R' is hydrogen and R" NH—$(CH_2)$n-C(=O)R''', with n being, for example, from 1 to 6, and R''' being hydrogen or alkyl or cycloalkyl or aryl; compounds in which R' is hydrogen and R" NH—$(CH_2)$n-CH(OR''')$_2$, with n being, for example, from 1 to 6, and R''' being hydrogen or alkyl or cycloalkyl or aryl; and compounds in which R' is hydrogen and R" NH—$(CH_2)$n-R''', with n being, for example, from 1 to 6, and R''' being hydrogen or alkyl or cycloalkyl or aryl or heteroaryl or heteroalicyclic.

In some of any of the embodiments described herein, $R_2$ is alkyl, and in some of these embodiments $R_2$ is a substituted alkyl, for example, an alkyl substituted by one or more amine groups (aminoalkyl).

In some of any of the embodiments described herein, and any combination thereof, the amine substituent at position 1 (Ring II) in Formula I, is a modified amine, as described herein, such that $R_4$ is other than hydrogen.

In some of these embodiments, $R_4$ can be alkyl, alkaryl, cycloalkyl, aryl, an acyl, or an amino-substituted α-hydroxy acyl, as defined herein, such as, for example, (S)-4-amino-2-hydroxybutyryl (AHB), or (S)-4-amino-2-hydroxypropionyl (AHP).

In some of the embodiments where $R_4$ is alkyl, the alkyl can be, for example, a lower alkyl, of 1-4 carbon atoms, such as, but not limited to, methyl, ethyl, propyl, butyl, isopropyl, and isobutyl, each being optionally substituted, as described herein.

In some of these embodiments, the alkyl is independently a non-substituted alkyl, such as, but not limited to, ethyl, propyl and isopropyl.

In some of these embodiments, the alkyl is independently a substituted methyl, such as, but not limited to, an alkaryl such as benzyl.

Alternatively, $R_4$ is cycloalkyl, and the cycloalkyl can be, for example, cyclopropyl, cyclobutyl, cyclopentyl and cyclohexyl.

Further alternatively, $R_4$ is aryl, and the aryl can be, for example, a substituted or unsubstituted phenyl. Non-limiting examples include unsubstituted phenyl and toluene.

In some of any of the embodiments described herein, $R_4$ is alkyl, cycloalkyl or aryl, as described herein.

In some of these embodiments, $R_1$ is alkyl, cycloalkyl or aryl, and is preferably alkyl, as defined herein.

In some of these embodiments, $R_1$ is alkyl, cycloalkyl or aryl, and is preferably alkyl, as defined herein, and $R_7$ is alkyl.

In some of any of the embodiments described herein, $R_4$ is alkyl and in some embodiments it is a lower alkyl, of 1-4 carbon atoms.

In some embodiments, $R_4$ is an alkyl such as ethyl, propyl, butyl, isopropyl, isobutyl, tert-butyl, each being optionally substituted.

In some embodiments, $R_4$ is methyl or ethyl, and is preferably a substituted methyl or ethyl. In some of these embodiments, the methyl or ethyl is substituted by, for example, a cycloalkyl or aryl. Such substituents are also referred to in the art as alkylcycloalkyl and alkaryl, respectively. An exemplary alkaryl is benzyl (—$CH_2$-Phenyl).

In some embodiments, $R_4$ is propyl or isopropyl.

In some embodiments, $R_4$ is benzyl.

In some of any of the embodiments described herein, $R_4$ is a cell-permealizable group, as defined herein, and in some embodiments, $R_4$ is guanidinyl.

In some of any of the embodiments described herein, $R_1$ is alkyl, cycloalkyl or aryl, and is preferably alkyl, as defined herein, and $R_4$ is alkyl, as defined herein, preferably, ethyl, propyl, isopropyl or benzyl.

In some of any of the embodiments described herein, $R_1$ is alkyl, cycloalkyl or aryl, and is preferably alkyl, as defined herein; $R_4$ is alkyl, as defined herein, preferably, ethyl, propyl, isopropyl or benzyl; and $R_7$ is alkyl.

In some of any of the embodiments described herein, $R_1$ is alkyl, cycloalkyl or aryl, and is preferably alkyl, as defined herein; $R_4$ is a cell-permealizing group, as defined herein, preferably, guanidine or guanine; and $R_7$ is alkyl.

In some of any of the embodiments described herein, $R_1$ is alkyl, cycloalkyl or aryl, and is preferably alkyl, as defined herein; and $R_4$ is a cell-permealizing group, as defined herein, preferably, guanidine or guanine, more preferably guanidine.

In some of any of the embodiments described herein, $R_4$ is hydrogen or a moiety such as (S)-4-amino-2-hydroxybutyryl (AHB), or (S)-4-amino-2-hydroxypropionyl (AHP).

In some of these embodiments, a modified amine is introduced to the compound within the third saccharide moiety (Ring III in Formula I).

In some of any of the embodiments described herein, is the third saccharide ting a pentose monosaccharide moiety as represented by Formula I. Alternatively, the monosaccharide moiety is hexose. Further alternatively, the monosaccharide moiety is other than pentose or hexose, for example, a hexose moiety as described in U.S. Pat. No. 3,897,412.

In some of any of the embodiments described herein, $R_5$ and $R_6$ are each hydrogen.

In some of these embodiments, $R_4$ is alkyl, cycloalkyl or aryl, and is preferably alkyl, as described herein.

In some embodiments, $R_1$ is alkyl, cycloalkyl or aryl, and is preferably alkyl, as defined herein; $R_4$ is alkyl, as defined herein, preferably, ethyl, propyl, isopropyl or benzyl; $R_5$ and $R_6$ are both hydrogen; and $R_7$ is alkyl, cycloalkyl or aryl, and is preferably alkyl, as defined herein.

In some of any of the embodiments described herein, $R_4$ is hydrogen, acyl or amino-substituted α-hydroxy-acyl, as defined herein.

In some of these embodiments, one of $R_5$ and $R_6$ is other than hydrogen. In some of these embodiments, one of $R_5$ and $R_6$ is a cell-permealizable group such as, for example, a guanidine group. Alternatively, one of $R_5$ and $R_6$ is acyl, alkyl, cycloalkyl or aryl, as defined, for example, for any of the embodiments of $R_4$.

In some of any of the embodiments described herein, $R_1$ is alkyl, cycloalkyl or aryl, and is preferably alkyl, as defined herein; $R_4$ is hydrogen or amino-substituted α-hydroxy-acyl, as defined herein; $R_5$ is a guanidine group (guanidinyl); and $R_7$ is alkyl, cycloalkyl or aryl, and is preferably alkyl, as defined herein.

In some of these embodiments, $R_6$ is hydrogen.

In some of any of the embodiments described herein for Formula I, $R_6$ is hydrogen or methyl, unless specifically indicated otherwise.

In some of any of the embodiments described herein for Formula I, $R_6$ is hydrogen.

In some of any of the embodiments described herein for Formula I, $R_5$ is acyl, as defined herein.

In some of any of the embodiments described herein for Formula I, one or both of $R_5$ and $R_6$ is a substituted or unsubstituted alkyl, a substituted or unsubstituted cycloalkyl, a substituted or unsubstituted aryl, a substituted or unsubstituted alkaryl, or a substituted or unsubstituted heteroaryl, as these terms are defined herein.

In some of any of the embodiments described herein for Formula I, $R_5$ and $R_6$ form together a nitrogen-containing heterocyclic ring, such as, but not limited to, morpholine, piperidine, and piperazine.

Figure 2:
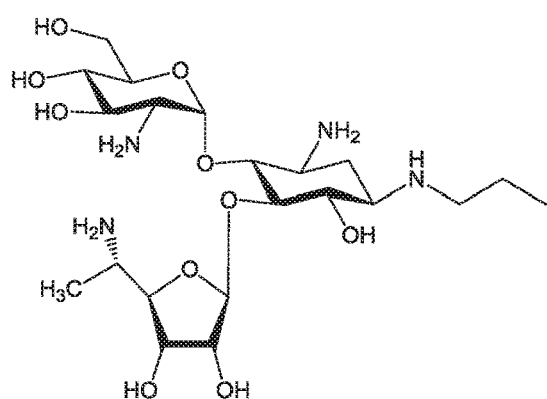
FIG. 2 presents the chemical structures of exemplary compounds according to some embodiments of the present invention.
Figure 2:
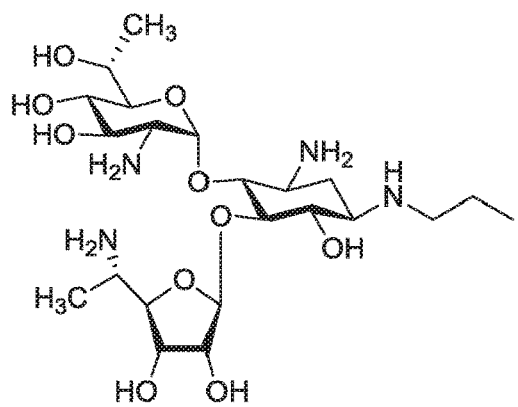
Figure 2:
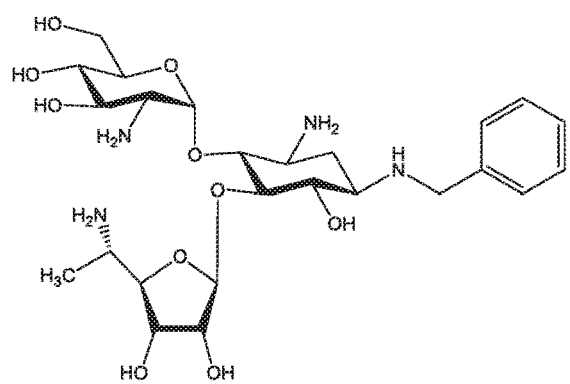
Figure 2:
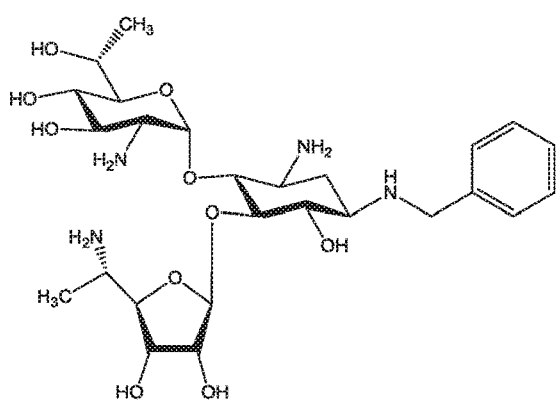
Figure 2:
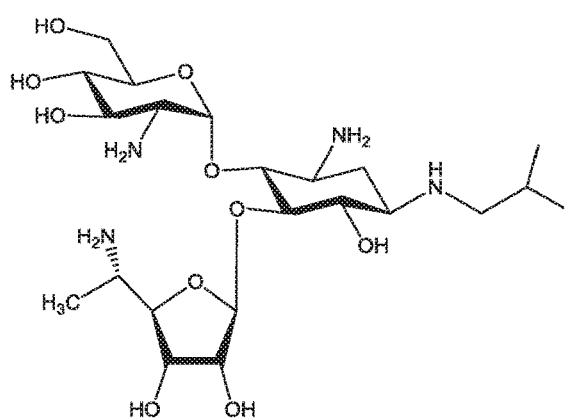
Figure 2:
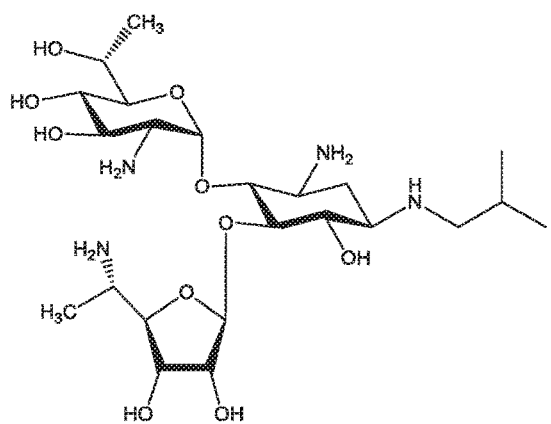

The chemical structures of exemplary compounds according to some embodiments of the present invention are presented in FIG. 2.

In some of any one of the embodiments described herein, and any combination thereof, the configuration at position 6' is an R-stereoconfiguration.

In some of any one of the embodiments described herein, and any combination thereof, the configuration at position 5" is an S-stereoconfiguration.

Herein throughout, the term "acyl" describes a —C(=O)—R group, with R being a substituted or unsubstituted alkyl, cycloalkyl, aryl, alkaryl, or hydrogen.

In exemplary embodiments, the acyl is such that R is an alkyl or alkaryl or aryl, each of which being optionally substituted by one or more amine substituents.

In some embodiments, the R is a substituted alkyl, and in some embodiments, R is substituted by hydroxy at the α position with respect to the carbonyl group, such that the acyl is α-hydroxy-acyl.

In some embodiments, the α-hydroxy-acyl is further substituted by one or more amine groups, and is an amino-substituted α-hydroxy-acyl.

In some of the embodiments of an acyl group as described herein, the amine substituents can be, for example, at one or more of positions β, γ, δ, and/or ω of the moiety R, with respect to the acyl.

Exemplary amino-substituted α-hydroxy-acyls include, without limitation, the moiety (S)-4-amino-2-hydroxybutyryl, which is also referred to herein as AHB. According to some embodiments of the present invention, an alternative to the AHB moiety can be the α-hydroxy-β-aminopropionyl (AHP) moiety. Additional exemplary amino-substituted α-hydroxy-acyls include, but are not limited to, L-(−)-γ-amino-α-hydroxybutyryl, L-(−)-δ-amino-α-hydroxyvaleryl, L-(−)-β-benzyloxycarbonylamino-α-hydroxypropionyl, a L-(−)-δ-benzyloxycarbonylamino-α-hydroxyvaleryl It is noted herein that according to some embodiments of the present invention, other moieties which involve a combination of carbonyl(s), hydroxyl(s) and amino group(s) along a lower alkyl exhibiting any stereochemistry, are contemplated as optional substituents in place of AHB and/or AHP, including, for example, 2-amino-3-hydroxybutanoyl, 3-amino-2-hydroxypentanoyl, 5-amino-3-hydroxyhexanoyl and the likes.

The chemical structures of exemplary compounds according to some embodiments of the present invention are presented in FIG. 2.

For any of the embodiments described herein, and any combination thereof, the compound may be in a form of a salt, for example, a pharmaceutically acceptable salt.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound. A pharmaceutically acceptable salt of a compound as described herein can alternatively be formed during the synthesis of the compound, e.g., in the course of isolating the compound from a reaction mixture or re-crystallizing the compound.

In the context of some of the present embodiments, a pharmaceutically acceptable salt of the compounds described herein may optionally be an acid addition salt comprising at least one basic (e.g., amine and/or guanidine) group of the compound which is in a positively charged form (e.g., wherein the basic group is protonated), in combination with at least one counter-ion, derived from the selected base, that forms a pharmaceutically acceptable salt.

The acid addition salts of the compounds described herein may therefore be complexes formed between one or more basic groups of the compound and one or more equivalents of an acid.

Depending on the stoichiometric proportions between the charged group(s) in the compound and the counter-ion in the salt, the acid additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

An example, without limitation, of a pharmaceutically acceptable salt would be an ammonium cation or guanidinium cation and an acid addition salt thereof.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined herein.

The present embodiments further encompass any enantiomers, diastereomers, prodrugs, solvates, hydrates and/or pharmaceutically acceptable salts of the compounds described herein.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems. In the context of the present embodiments, a compound may exhibit one or more chiral centers, each of which exhibiting an R- or an S-configuration and any combination, and compounds according to some embodiments of the present invention, can have any their chiral centers exhibit an R- or an S-configuration.

The term "diastereomers", as used herein, refers to stereoisomers that are not enantiomers to one another. Diastereomerism occurs when two or more stereoisomers of a compound have different configurations at one or more, but not all of the equivalent (related) stereocenters and are not mirror images of each other. When two diastereoisomers differ from each other at only one stereocenter they are epimers.

Each stereo-center (chiral center) gives rise to two different configurations and thus to two different stereoisomers. In the context of the present invention, embodiments of the present invention encompass compounds with multiple chiral centers that occur in any combination of stereo-configuration, namely any diastereomer.

According to some of any of the embodiments described herein, a stereo-configuration of each of position 6' and position 5" is independently an R configuration or an S configuration.

According to some of any of the embodiments described herein, a stereo-configuration of position 6' is an R configuration.

According to some of any of the embodiments described herein, a stereo-configuration of position 5" is an S configuration.

According to some of any of the embodiments described herein, a stereo-configuration of position 6' is an R configuration and a stereo-configuration of position 5" is an R configuration or an S configuration.

According to some of any of the embodiments described herein, a stereo-configuration of position 6' is an R configuration and a stereo-configuration of position 5" is an S configuration.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester (the "prodrug"). Such a prodrug is hydrolyzed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the compound of the present invention) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

The terms "hydroxyl" or "hydroxy", as used herein, refer to an —OH group.

As used herein, the term "amine" describes a —NR'R" group where each of R' and R" is independently as described herein, and is, for example, hydrogen, alkyl, cycloalkyl, heteroalicyclic, aryl or heteroaryl, as these terms are defined herein. An amine in which one of R' and R" is other than hydrogen is referred to herein as "modified amine".

As used herein, the term "alkyl" describes an aliphatic hydrocarbon including straight chain and branched chain groups. The alkyl may have 1 to 20 carbon atoms, or 1-10 carbon atoms, and may be branched or unbranched. According to some embodiments of the present invention, the alkyl is a low (or lower) alkyl, having 1 to 6, or 1 to 4, carbon atoms (namely, methyl, ethyl, propyl and butyl).

Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. In some embodiments, the alkyl is a lower alkyl, including 1-6 or 1-4 carbon atoms.

An alkyl can be substituted or unsubstituted. When substituted, the substituent can be, for example, one or more of an alkyl (forming a branched alkyl), an alkenyl, an alkynyl, a cycloalkyl, an aryl, a heteroaryl, a heteroalicyclic, a halo, a trihaloalkyl, a hydroxy, an alkoxy and a hydroxyalkyl as these terms are defined hereinbelow. An alkyl substituted by aryl is also referred to herein as "alkaryl", an example of which is benzyl.

Whenever "alkyl" is described, it can be replaced also by alkenyl or alkynyl. The term "alkyl" as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond, e.g., allyl, vinyl, 3-butenyl, 2-butenyl, 2-hexenyl and i-propenyl. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "cycloalkyl" refers to an all-carbon monocyclic or fused ring (i.e., rings which share an adjacent pair of carbon atoms), branched or unbranched group containing 3 or more carbon atoms where one or more of the rings does not have a completely conjugated pi-electron system, and may further be substituted or unsubstituted. Exemplary cycloalkyl groups include, for example, cyclopropyl, cyclobutyl, cyclopentyl, cyclohexyl, or cyclododecyl. The cycloalkyl can be substituted or unsubstituted. When substituted, the substituent can be, for example, one or more of an alkyl, an alkenyl, an alkynyl, a cycloalkyl, an aryl, a heteroaryl, a heteroalicyclic, a halo, a trihaloalkyl, a hydroxy, an alkoxy and a hydroxyalkyl as these terms are defined hereinbelow.

The term "aryl" describes an all-carbon monocyclic or fused-ring polycyclic (i.e., rings which share adjacent pairs of carbon atoms) groups having a completely conjugated pi-electron system. The aryl group may be unsubstituted or substituted by one or more substituents. When substituted, the substituent can be, for example, one or more of an alkyl, an alkenyl, an alkynyl, a cycloalkyl, an aryl, a heteroaryl, a heteroalicyclic, a halo, a trihaloalkyl, a hydroxy, an alkoxy and a hydroxyalkyl as these terms are defined hereinbelow.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. Representative examples are thiadiazole, pyridine, pyrrole, oxazole, indole, purine and the like. The heteroaryl group may be unsubstituted or substituted by one or more substituents. When substituted, the substituent can be, for example, one or more of an alkyl, an alkenyl, an alkynyl, a cycloalkyl, an aryl, a heteroaryl, a heteroalicyclic, a halo, a trihaloalkyl, a hydroxy, an alkoxy and a hydroxyalkyl as these terms are defined hereinbelow.

The term "heteroalicyclic", as used herein, describes a monocyclic or fused ring group having in the ring(s) one or more atoms such as nitrogen, oxygen and sulfur. The rings may also have one or more double bonds. However, the rings do not have a completely conjugated pi-electron system. Representative examples are morpholine, piperidine, piperazine, tetrahydrofurane, tetrahydropyrane and the like. The heteroalicyclic may be substituted or unsubstituted. When substituted, the substituent can be, for example, one or more of an alkyl, an alkenyl, an alkynyl, a cycloalkyl, an aryl, a heteroaryl, a heteroalicyclic, a halo, a trihaloalkyl, a hydroxy, an alkoxy and a hydroxyalkyl as these terms are defined hereinbelow.

The term "halide", as used herein, refers to the anion of a halo atom, i.e. $F^-$, $Cl^-$, $Br^-$ and $I^-$.

The term "halo" refers to F, Cl, Br and I atoms as substituents.

The term "alkoxide" refers to an R'—O$^-$ anion, wherein R' is as defined hereinabove.

The term "alkoxy" refers to an OR' group, wherein R' is as defined herein, but other than hydrogen.

The term "hydroxyalkyl," as used herein, refers to an alkyl group, as defined herein, substituted with one or more hydroxy group(s), e.g., hydroxymethyl, 2-hydroxyethyl and 4-hydroxypentyl.

The term "aminoalkyl," as used herein, refers to an alkyl group, as defined herein, substituted with one or more amino group(s).

The term "alkoxyalkyl," as used herein, refers to an alkyl group substituted with one alkoxy group, e.g., methoxymethyl, 2-methoxyethyl, 4-ethoxybutyl, n-propoxyethyl and t-butylethyl.

The term "trihaloalkyl" refers to —CX$_3$, wherein X is halo, as defined herein. An exemplary haloalkyl is CF$_3$.

A "guanidino" or "guanidine" or "guanidinyl" group refers to an —RaNC(=NRd)-NRbRc group, where each of Ra, Rb, Re and Rd can be as defined herein for R' and R".

A "guanyl" or "guanine" group refers to an RaRbNC (=NRd)- group, where Ra, Rb and Rd are as defined herein.

In some of any of the embodiments described herein, the guanidine group is —NH—C(=NH)—NH$_2$.

In some of any of the embodiments described herein, the guanyl group is H$_2$N—C(=NH)— group.

Any one of the amine (including modified amine), guanidine and guanine groups described herein is presented as a free base form thereof, but is meant to encompass an ionized form thereof at physiological pH, and/or within a salt thereof, e.g., a pharmaceutically acceptable salt thereof, as described herein.

For any one of the alkyl, cycloalkyl, aryl, alkaryl, heteroaryl, heteroalicyclic, and acyl described herein, alternative substituents include, but are not limited to, sulfonate, sulfoxide, thiosulfate, sulfate, sulfite, thiosulfite, phosphonate, thiohydroxy, thioalkoxy, thioaryloxy, cyano, nitro, azo, sulfonamide, carbonyl, thiocarbonyl, C-carboxylate, O-carboxylate, N-thiocarbamate, O-thiocarbamate, oxo, thiooxo, oxime, acyl, acyl halide, azo, azide, urea, thiourea, N-carbamate, O-carbamate, C-amide, N-amide, hydrazine and hydrazide, as these terms are defined herein.

The term "cyano" describes a —C≡N group.

The term "nitro" describes an —NO$_2$ group.

The term "sulfate" describes a —O—S(=O)$_2$—OR' end group, as this term is defined hereinabove, or an —O—S (=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" describes a —S(=O)—OR' end group or an —S(=O)—O— group linking group, as these phrases are defined hereinabove, where R' is as defined hereinabove.

The term "sulfoxide" or "sulfinyl" describes a —S(=O) R' end group or an —S(=O)— linking group, as these phrases are defined hereinabove, where R' is as defined hereinabove.

The term "sulfonate" describes a —S(=O)$_2$—R' end group or an —S(=O)$_2$— linking group, as these phrases are defined hereinabove, where R' is as defined herein.

The term "S-sulfonamide" describes a —S(=O)$_2$—NR'R" end group or a —S(=O)$_2$—NR'— linking group, as these phrases are defined hereinabove, with R' and R" as defined herein.

The term "N-sulfonamide" describes an R'S(=O)$_2$—NR"— end group or a —S(=O)$_2$—NR'— linking group, as these phrases are defined hereinabove, where R' and R" are as defined herein.

The term "carbonyl" or "carbonate" as used herein, describes a —C(=O)—R' end group or a —C(=O)— linking group, as these phrases are defined hereinabove, with R' as defined herein.

The term "thiocarbonyl" as used herein, describes a —C(=S)—R' end group or a —C(=S)— linking group, as these phrases are defined hereinabove, with R' as defined herein.

The term "oxo" as used herein, describes a (=O) group, wherein an oxygen atom is linked by a double bond to the atom (e.g., carbon atom) at the indicated position.

The term "thiooxo" as used herein, describes a (=S) group, wherein a sulfur atom is linked by a double bond to the atom (e.g., carbon atom) at the indicated position.

The term "oxime" describes a =N—OH end group or a =N—O— linking group, as these phrases are defined hereinabove.

The term "acyl halide" describes a —(C=O)R"" group wherein R"" is halide, as defined hereinabove.

The term "azo" or "diazo" describes an —N=NR' end group or an —N=N— linking group, as these phrases are defined hereinabove, with R' as defined hereinabove.

The term "azide" describes an —N$_3$ end group.

The term "carboxylate" as used herein encompasses C-carboxylate and O-carboxylate.

The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)— linking group, as these phrases are defined hereinabove, where R' is as defined herein.

A carboxylate can be linear or cyclic. When cyclic, R' and the carbon atom are linked together to form a ring, in C-carboxylate, and this group is also referred to as lactone. Alternatively, R' and O are linked together to form a ring in O-carboxylate. Cyclic carboxylates can function as a linking group, for example, when an atom in the formed ring is linked to another group.

The term "thiocarboxylate" as used herein encompasses C-thiocarboxylate and O-thiocarboxylate.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)— linking group, as these phrases are defined hereinabove, where R' is as defined herein.

A thiocarboxylate can be linear or cyclic. When cyclic, R' and the carbon atom are linked together to form a ring, in C-thiocarboxylate, and this group is also referred to as thiolactone. Alternatively, R' and O are linked together to form a ring in O-thiocarboxylate. Cyclic thiocarboxylates can function as a linking group, for example, when an atom in the formed ring is linked to another group.

The term "carbamate" as used herein encompasses N-carbamate and O-carbamate.

The term "N-carbamate" describes an R"OC(=O)—NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

A carbamate can be linear or cyclic. When cyclic, R' and the carbon atom are linked together to form a ring, in O-carbamate. Alternatively, R' and O are linked together to form a ring in N-carbamate. Cyclic carbamates can function as a linking group, for example, when an atom in the formed ring is linked to another group.

The term "carbamate" as used herein encompasses N-carbamate and O-carbamate.

The term "thiocarbamate" as used herein encompasses N-thiocarbamate and O-thiocarbamate.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'— linking group, as these phrases are defined hereinabove, with R' and R" as defined herein.

Thiocarbamates can be linear or cyclic, as described herein for carbamates.

The term "dithiocarbamate" as used herein encompasses S-dithiocarbamate and N-dithiocarbamate.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking group, with R', R" and R'" as defined herein.

The term "amide" as used herein encompasses C-amide and N-amide.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

The term "hydrazine" describes a —NR'—NR"R'" end group or a —NR'—NR"— linking group, as these phrases are defined hereinabove, with R', R", and R'" as defined herein.

As used herein, the term "hydrazide" describes a —C(=O)—NR'—NR"R'" end group or a —C(=O)—NR'—NR"— linking group, as these phrases are defined hereinabove, where R', R" and R'" are as defined herein.

As used herein, the term "thiohydrazide" describes a —C(=S)—NR'—NR"R'" end group or a —C(=S)—NR'—NR"— linking group, as these phrases are defined hereinabove, where R', R" and R'" are as defined herein.

Further according to embodiments of the present invention, there are provided processes of preparing the compounds as described herein.

These processes are generally effected by devising appropriate aminoglycoside acceptor molecules and corresponding donor molecules, as is known in the art of aminoglycosides.

Generally, the synthesis of compounds according to some embodiments of the present invention is accomplished using suitable acceptor and donor molecules and reaction conditions which allow reacting a protected derivative of the donor and of the acceptor and removing the protecting group so as to obtain a desired pseudo-trisaccharide.

The term "acceptor" is used herein to describe the skeletal structure derived from paromamine which has an available (unprotected) hydroxyl group at position C5, which is reactive during a glycosylation reaction, and can accept a glycosyl.

The term "donor" is used herein to describe the glycosyl that reacts with the acceptor to form the final pseudo-trisaccharide compound.

The term "glycosyl", as used herein, refers to a chemical group which is obtained by removing the hydroxyl group from the hemiacetal function of a monosaccharide.

The term "monosaccharide", as used herein and is well known in the art, refers to a simple form of a sugar that consists of a single saccharide molecule which cannot be further decomposed by hydrolysis. The monosaccharide according to embodiments of the present invention is a ribose. When classified according to the number of carbon atoms of the carbohydrate, the monosaccharide is a pentose, having 5 carbon atoms.

The donors and acceptors are designed so as to form the desired compounds according to some embodiments of the present invention. The following describes some embodiments of this aspect of the present invention, presenting exemplary processes of preparing exemplary subsets of the compounds described herein. More detailed processes of preparing exemplary compounds according to some embodiments of the present invention, are presented in the Examples section that follows below.

The syntheses of the compounds according to some embodiments of the present invention, generally include (i) preparing an acceptor compound by selective protection of one or more hydroxyls and amines at selected positions present on the paromamine scaffold, leaving the selected position (C5) unprotected and therefore free to accept a donor (glycosyl) compound as defined herein; (ii) preparing a donor compound by selective protection of one or more hydroxyls and amines at selected positions present on the glycosyl, leaving one position unprotected and therefore free to couple with an acceptor compound as defined herein; (iii) subjecting the donor and the acceptor to a coupling reaction; and (iii) removing the protecting groups to thereby obtain the desired compound.

The phrase "protected group", as used herein, refers to a group that is substituted or modified so as to block its functionality and protect it from reacting with other groups under the reaction conditions (e.g., a coupling reaction as described herein). A protected group is re-generated by removal of the substituent or by being re-modified.

When an "amino-protected group" or "hydroxyl-protected group" are used, it is meant that a protecting group is attached or used to modify the respective group so as to generate the protected group.

The phrase "protecting group", as used herein, refers to a substituent or a modification that is commonly employed to block or protect a particular functionality while reacting other functional groups on the compound. The protecting group is selected so as to release the substituent or to be re-modified, to thereby generate the desired unprotected group.

For example, an "amino-protecting group" or "amine-protecting group" is a substituent attached to an amino group, or a modification of an amino group, that blocks or protects the amino functionality in the compound, and prevents it from participating in chemical reactions. The amino-protecting group is removed by removal of the substituent or by a modification that re-generates an amine group.

Suitable amino-protected groups include azide (azido), N-phthalimido, N-acetyl, N-trifluoroacetyl, N-t-butoxycarbonyl (BOC), N-benzyloxycarbonyl (CBz) and N-9-fluorenylmethylenoxycarbonyl (Fmoc).

A "hydroxyl-protecting group" or "hydroxyl-protecting group" refers to a substituent or a modification of a hydroxyl group that blocks or protects the hydroxyl functionality, and prevents it from participating in chemical reactions. The hydroxy-protecting group is removed by removal of the substituent or by a modification that re-generates a hydroxy group.

Suitable hydroxy protected groups include isopropylidene ketal and cyclohexanone dimethyl ketal (forming a 1,3-dioxane with two adjacent hydroxyl groups), 4-methoxy-1-methylbenzene (forming a 1,3-dioxane with two adjacent hydroxyl groups), O-acetyl, O-chloroacetyl, O-benzoyl and O-silyl.

For a general description of protecting groups and their use, see T. W. Greene, Protective Groups in Organic Synthesis, John Wiley & Sons, New York, 1991.

According to some embodiments, the amino-protected groups include an azido ($N_3$—) and/or an N-phthalimido group, and the hydroxyl-protecting groups include O-acetyl (AcO—), O-benzoyl (BzO—) and/or O-chloroacetyl.

It is noted herein that when applicable, a "protected group" refers to a moiety in which one reactive function on a compound is protected or more than one function are protected at the same time, such as in the case of two adjacent functionalities, e.g., two hydroxyl groups that can be protected at once by a isopropylidene ketal.

In some embodiments, the donor compound is a protected monosaccharide which can be represented by the general Formula III, having a leaving group at position 1" thereof, denoted L, and a substituent $R_8$ at position 5", as defined herein:

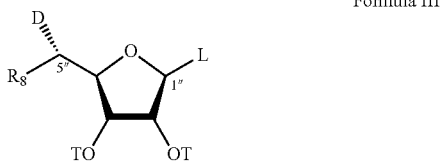

Formula III wherein:
L is a leaving group;
OT is a donor protected hydroxyl group;
$R_8$ is as defined herein for $R_7$ in Formula I (the configuration at the 5" position as presented in Formula IV being a non-limiting example); and
D is a protected or unprotected form of $NR_5R_6$ as defined for Formula I, wherein when $R_5$ and $R_6$ are both hydrogen, D is a donor protected amine group.

As used herein, the phrase "leaving group" describes a labile atom, group or chemical moiety that readily undergoes detachment from an organic molecule during a chemical reaction, while the detachment is typically facilitated by the relative stability of the leaving atom, group or moiety thereupon. Typically, any group that is the conjugate base of a strong acid can act as a leaving group. Representative examples of suitable leaving groups according to some of the present embodiments include, without limitation, trichloroacetimidate, acetate, tosylate, triflate, sulfonate, azide, halide, hydroxy, thiohydroxy, alkoxy, cyanate, thiocyanate, nitro and cyano.

According to some embodiments of the present invention, each of the donor hydroxyl-protecting groups is O-benzoyl and the donor amino-protecting group in either $R_5$ or $R_6$ is azido, although other protecting groups are contemplated.

It is to be noted that when one of $R_5$ and $R_6$ is other than hydrogen, it can be protected or unprotected. Typically, when one of $R_5$ and $R_6$ is guanine or guanidine, a protecting group suitable for the reaction conditions (e.g., of a coupling reaction with an acceptor) can be used. Optionally, the guanine or guanidine are unprotected. When one of $R_5$ and $R_6$ is an alkyl, aryl or cycloalkyl, typically D in Formula III is an unprotected form of $NR_6R_7$.

The structure of the donor compound sets the absolute structure of Ring III in the resulting compound according to some embodiments of the present invention, namely the stereo-configuration of the 5" position and the type of $R_5$, $R_6$ and $R_7$ in Formula I.

Exemplary acceptor molecules suitable for use in the preparation of the compounds described herein, are represented by Formula IV:

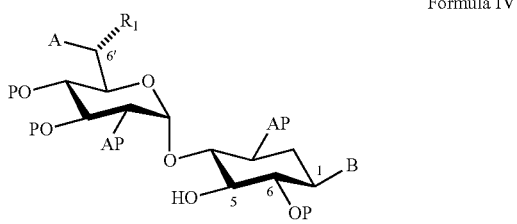

Formula IV wherein:

the dashed line represents an S-configuration or an R-configuration at position 6';

OP is an acceptor protected hydroxyl group;

AP is an acceptor protected amine group;

$R_1$ is as defined herein for Formula I;

A is an acceptor protected hydroxyl group (OP), in case $R_2$ in Formula I is OH; an acceptor protected amine group (AP), in case $R_2$ is Formula I is $NH_2$; or can otherwise be one of the other groups defining $R_2$, either protected or unprotected, according to the chemical nature of these groups and the reaction conditions; and B is an acceptor protected amine group, in case $R_4$ is Formula I is hydrogen, or can otherwise be a protected or unprotected form of the groups defining $R_4$.

According to some embodiments of the present invention, the acceptor hydroxyl-protected group is O-acetyl.

According to some embodiments of the present invention, the donor amino-protecting group is azido, although other protecting groups are contemplated.

The acceptor hydroxyl-protected groups and the acceptor amino-protected groups at the various positions of the acceptors can be the same or different each position.

In some embodiments, for example, in case $R_4$ is other than H, the acceptor is prepared by generating the moiety B, prior to reacting it with the donor.

The structure of the acceptor compound sets the absolute structure of Ring I and Ring II in the resulting compound according to some embodiments of the present invention.

Exemplary processes are described the Examples section that follows.

Embodiments of the present invention further encompass any of the intermediate compounds described herein for preparing the compounds of the present embodiments.

Therapeutic Uses:

The compounds presented herein were designed so as to possess a truncation mutation suppression activity, namely the ability to induce readthrough of a premature stop codon mutation. Such an activity renders these compounds suitable for use as therapeutically active agents for the treatment of genetic disorders, and particularly such disorders which are characterized by a truncation mutation.

As known in the art, about a third of alleles causing genetic diseases carry premature termination (stop) codons (PTCs), which lead to the production of truncated proteins. One possible therapeutic approach involves the induction and/or promotion of readthrough of such PTCs to enable synthesis of full-length proteins. PTCs originate from either mutations, such as nonsense mutations, frame-shift deletions and insertions, or from aberrant splicing that generates mRNA isoforms with truncated reading frames. These mutations can lead to the production of truncated, nonfunctional or deleterious proteins, owing to dominant negative or gain-of-function effects.

In general, readthrough of PTCs can be achieved by suppressor transfer RNAs (tRNAs), factors that decrease translation-termination efficiency, such as small-interfering RNAs (siRNAs) directed against the translation-termination factors, and RNA antisense that targets the nonsense mutation region. One of the objectives of the present invention is to provide a pharmacological therapeutic approach aimed at achieving sufficient levels of functional proteins in a subject suffering from at least one genetic disorder associated with at least one premature stop-codon mutation. According to embodiments of the present invention, the provided therapeutic approach is aimed at inducing and/or promoting translational readthrough of the disease causing PTCs, to enable the synthesis and expression of full-length functional proteins.

As presented hereinabove, one extensively studied approach that has reached clinical trials, is based on readthrough by drugs affecting the ribosome decoding site, such as aminoglycoside antibiotics; however, aminoglycosides have severe adverse side effects when used at high concentrations and/or used long-term. The compounds presented herein were designed to exhibit an ability to induce and/or promote readthrough of a premature stop-codon mutation in an organism having such a mutation, while exhibiting minimal adverse effects. Such an activity renders these compounds suitable for use as therapeutically active agents for the treatment of genetic disorders associated with a premature stop-codon mutation.

According to an aspect of some embodiments of the present invention, any of the compounds presented herein having Formula I or Ia, including any of the respective embodiments of the compounds and any combinations thereof, are for use in inducing and/or promoting readthrough of a premature stop codon mutation and/or for increasing an expression of a gene having a premature stop codon mutation, and/or are for use in the manufacture of a medicament for inducing and/or promoting readthrough of a premature stop codon mutation and/or for increasing an expression of a gene having a premature stop codon mutation.

According to an aspect of some embodiments of the present invention there is provided a method of inducing and/or promoting readthrough of a premature stop codon mutation and/or for increasing an expression of a gene having a premature stop codon mutation, which is effected by translating a gene having a premature stop codon mutation into a protein in the presence of a compound as described herein in any of the respective embodiments and any combination thereof.

Any of the premature stop-codon mutations are contemplated. In some embodiments, the mutations are those having an RNA code of UGA, UAG or UAA.

According to some of any of the embodiments described herein, the protein is translated in a cytoplasmic translation system.

According to some of any of the embodiments described herein, the compound is used in a mutation suppression amount.

According to some of any of the embodiments described herein, an inhibition of translation $IC_{50}$ of the compound in a eukaryotic cytoplasmic translation system is greater that an inhibition of translation $IC_{50}$ of the compound in a ribosomal translation system.

According to some of any of the embodiments described herein, an inhibition of translation $IC_{50}$ of the compound in a eukaryotic cytoplasmic translation system is greater that an inhibition of translation $IC_{50}$ of the compound in a prokaryotic translation system.

According to an aspect of some embodiments of the present invention, any of the compounds presented herein having Formula I or Ia, including any of the respective embodiments of the compounds and any combinations thereof, are for use in the treatment of a genetic disorder associated with a premature stop-codon mutation, or for use in the manufacture of a medicament for the treatment of a genetic disorder associated with a premature stop-codon mutation.

According to an aspect of some embodiments of the present invention there is provided a method of treating a genetic disorder associated with a premature stop-codon mutation. The method, according to this aspect of the present invention, is effected by administering to a subject in need thereof a therapeutically effective amount of one or more of the compounds presented herein having Formula Ia or Ib, including any of the respective embodiments of the compounds and any combinations thereof.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the phrase "therapeutically effective amount" describes an amount of the polymer being administered which will relieve to some extent one or more of the symptoms of the condition being treated.

The phrase "genetic disorder", as used herein, refers to a chronic disorder which is caused by one or more defective genes that are often inherited from the parents, and which can occur unexpectedly when two healthy carriers of a defective recessive gene reproduce, or when the defective gene is dominant. Genetic disorders can occur in different inheritance patterns which include the autosomal dominant pattern wherein only one mutated copy of the gene is needed for an offspring to be affected, and the autosomal recessive pattern wherein two copies of the gene must be mutated for an offspring to be affected.

The phrase "genetic disorder", as used herein, encompasses a genetic disorder, genetic disease, genetic condition or genetic syndrome.

According to some of any of the embodiments of the present invention, the genetic disorder, genetic disease, genetic condition or genetic syndrome, involves a gene having a premature stop-codon mutation, also referred to herein as a truncation mutation and/or a nonsense mutation, which leads to improper translation thereof. The improper translation produces a dysfunctional essential protein or causes a reduction or abolishment of synthesis of an essential protein. In the context of the some embodiments of the present invention, the genetic disorders which are contemplated within the scope of the present embodiments are referred to as genetic disorders associated with a premature stop-codon mutation and/or a protein truncation phenotype.

According to some of any of the embodiments of the present invention, a genetic disorder associated with a premature stop-codon mutation and/or a protein truncation phenotype is treatable by inducing and/or promoting readthrough of the mutation in the complete but otherwise defective transcript (mRNA), or in other words, by inducing and/or promoting suppression of the nonsense mutation (the premature stop-codon mutation and/or the truncation mutation). In the context of embodiments of the present invention, a genetic disorder is one that is treatable by readthrough-inducing and/or promoting compounds.

Methods for identification of a genetic disorder associated with a premature stop-codon mutation and/or a protein truncation phenotype are well known in the art, and include full or partial genome elucidation, genetic biomarker detection, phenotype classification and hereditary information analysis.

Such methods often result in pairs of mutant/wild type (WT) sequences, and these pairs can be used in known methodologies for identifying if the genetic disorder is associated with a premature stop-codon mutation and/or a protein truncation phenotype.

A readthrough-inducing/promoting activity of compounds for treating such genetic disorders can be established by methods well known in the art.

For example, a plasmid comprising two reporter genes interrupted by a sequence of the mutated gene (the genetic disorder-causing gene) is transected into a protein expression platform, either in full cells or in a cell-free systems, and the ratio between the expression level of the two genes in the presence of a tested compound is measured, typically in series of concentrations and duplications, and compared to the gene expression level ratio of the wild-type and/or to the expression level ratio measured in a control sample not containing the tested compound.

It is noted that the experimental model for readthrough activity, namely the nucleotide sequence of gene containing the premature stop-codon mutation, is a byproduct of the process of identifying a genetic disorder as associated with a premature stop-codon mutation and/or a protein truncation phenotype, and further noted that with the great advances in genomic data acquisition, this process is now well within the skills of the artisans of the art, and that once the mechanism of action of a drug candidate is established, as in the case of genetic disorders which have been shown to be associated with a premature stop-codon mutation and/or a protein truncation phenotype, it is well within the skills of the artisans of the art to identify, characterize and assess the efficacy, selectivity and safety of any one of the readthrough-inducing compounds presented herein. It is further well within the skills of the artisans of the art to take the readthrough-inducing compounds presented herein further though the routine processes of drug development.

Methodologies for testing readthrough of a premature stop-codon mutation and/or a truncation mutation, referred to herein as readthrough activity, are known in the art, and several exemplary experimental methods are provided in the Examples section that follows, by which the readthrough-inducing compounds, according to some embodiments of the present invention, can be characterized. It is to be understood that other methods can be used to characterized readthrough-inducing compounds, and such methods are also contemplated within the scope of the present invention. Methods such as provided herein can also be adapted for high throughput screening technology that can assay thousands of compounds in a relatively short period of time.

The skilled artisan would appreciate that many in vitro methodologies can be used to characterize readthrough-inducing compounds provided herein in terms of safety of use as drugs, and assess the drug candidates in terms of their cytotoxicity versus their efficacy. The skilled artisan would also appreciate that many in vitro methodologies can be used to characterize the readthrough-inducing compounds provided herein for eukaryotic versus prokaryotic selectivity, and such methodologies may also be adapted for high throughput screening technology that can assay thousands of compounds in a relatively short period of time.

Non-limiting examples of genetic disorders, diseases, conditions and syndromes, which are associated with the presence of at least one premature stop-codon or other nonsense mutations include cancer, Rett syndrome, cystic fibrosis (CF), Becker's muscular dystrophy (BMD), Congenital muscular dystrophy (CMD), Duchenne muscular dystrophy (DMD), Factor VII deficiency, Familial atrial fibrillation, Hailey-Hailey disease, hemophilia A, hemophilia B, Hurler syndrome, Louis-Bar syndrome (ataxia-telangiectasia, AT), McArdle disease, Mucopolysaccharidosis, Nephropathic cystinosis, Polycystic kidney disease, type I, II and III Spinal muscular atrophy (SMA), Tay-Sachs disease, Usher syndrome, cystinosis, Severe epidermolysis bullosa, Dravet syndrome, X-linked nephrogenic diabetes insipidus (XNDI) and X-linked retinitis pigmentosa.

Additional genetic disorders, diseases, conditions and syndromes, which are associated with the presence of at least one premature stop-codon or other nonsense mutations, are listed in "*Suppression of nonsense mutations as a therapeutic approach to treat genetic diseases*" by Kim M. Keeling, K. M Bedwell, D. M., *Wiley Interdisciplinary Reviews: RNA,* 2011, 2(6), p. 837-852; "*Cancer syndromes and therapy by stop-codon readthrough*", by Bordeira-Carriço, R. et al., *Trends in Molecular Medicine,* 2012, 18(11), p. 667-678, and any references cited therein, all of which are incorporated herewith by reference in their entirety.

In some of any of the embodiments described herein, the genetic disorder is Rett syndrome.

In any of the methods and uses described herein, the compounds described herein can be utilized either per se or form a part of a pharmaceutical composition, which further comprises a pharmaceutically acceptable carrier, as defined herein.

According to an aspect of some embodiments of the present invention, there is provided a pharmaceutical composition which comprises, as an active ingredient, any of the novel compounds described herein and a pharmaceutically acceptable carrier.

As used herein a "pharmaceutical composition" refers to a preparation of the compounds presented herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the compounds presented herein into preparations which, can be used pharmaceutically. Proper formulation is dependent upon the route of administration chosen.

According to some embodiments, the administration is effected orally. For oral administration, the compounds presented herein can be formulated readily by combining the compounds with pharmaceutically acceptable carriers well known in the art. Such carriers enable the compounds presented herein to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the compounds presented herein may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For injection, the compounds presented herein may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active aminoglicoside compounds doses.

For buccal administration, the compositions may take the form of tablets or lozenges formulated in conventional manner.

For administration by inhalation, the compounds presented herein are conveniently delivered in the form of an aerosol spray presentation (which typically includes powdered, liquefied and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compounds presented herein and a suitable powder base such as, but not limited to, lactose or starch.

The compounds presented herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the compounds preparation in water-soluble form. Additionally, suspensions of the compounds presented herein may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds presented herein to allow for the preparation of highly concentrated solutions.

Alternatively, the compounds presented herein may be in powder form for constitution with a suitable vehicle, e.g., sterile, pyrogen-free water, before use.

The compounds presented herein may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of compounds presented herein effective to prevent, alleviate or ameliorate symptoms of the disorder, or prolong the survival of the subject being treated.

Determination of a therapeutically effective amount is well within the capability of those skilled in the art, especially in light of the detailed disclosure provided herein.

For any compounds presented herein used in the methods of the present embodiments, the therapeutically effective amount or dose can be estimated initially from activity assays in animals. For example, a dose can be formulated in animal models to achieve a circulating concentration range that includes the mutation suppression levels as determined by activity assays (e.g., the concentration of the test compounds which achieves a substantial read-through of the truncation mutation). Such information can be used to more accurately determine useful doses in humans.

Toxicity and therapeutic efficacy of the compounds presented herein can be determined by standard pharmaceutical procedures in experimental animals, e.g., by determining the $EC_{50}$ (the concentration of a compound where 50% of its maximal effect is observed) and the $LD_{50}$ (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the compounds presented herein which are sufficient to maintain the desired effects, termed the minimal effective concentration (MEC). The MEC will vary for each preparation, but can be estimated from in vitro data; e.g., the concentration of the compounds necessary to achieve 50-90% expression of the whole gene having a truncation mutation, i.e. read-through of the mutation codon. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the chronic condition to be treated, dosing can also be a single periodic administration of a slow release composition described hereinabove, with course of periodic treatment lasting from several days to several weeks or until sufficient amelioration is effected during the periodic treatment or substantial diminution of the disorder state is achieved for the periodic treatment.

The amount of a composition to be administered will, of course, be dependent on the subject being treated, the severity of the affliction, the manner of administration, the judgment of the prescribing physician, etc. Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a compound according to the present embodiments, formulated in a compatible pharmaceutical carrier may also be prepared, placed in an appropriate container, and labeled for treatment of an indicated condition or diagnosis, as is detailed hereinabove.

Thus, in some embodiments, the pharmaceutical composition is packaged in a packaging material and identified in print, in or on the packaging material, for use in the treatment of a genetic disorder, as defined herein, and/or in any of the uses described herein.

In some embodiments, the pharmaceutical composition is for use in the treatment of a genetic disorder, as defined herein, and/or in any of the uses described herein. In any of the composition, methods and uses described herein, the compounds can be utilized in combination with other agents useful in the treatment of the genetic disorder and/or in inducing or promoting readthrough activity of a premature stop codon mutation and/or in increasing expression of a gene having a premature stop codon mutation as described herein.

Being primarily directed at treating genetic disorders, which are chronic by definition, the compounds presented herein or pharmaceutical compositions containing the same are expected to be administered throughout the lifetime of the subject being treated. Therefore, the mode of administration of pharmaceutical compositions containing the compounds should be such that will be easy and comfortable for administration, preferably by self-administration, and such that will take the smallest toll on the patient's wellbeing and course of life.

The repetitive and periodic administration of the compounds presented herein or the pharmaceutical compositions containing the same can be effected, for example, on a daily basis, i.e. once a day, more preferably the administration is effected on a weekly basis, i.e. once a week, more preferably the administration is effected on a monthly basis, i.e. once a month, and most preferably the administration is effected once every several months (e.g., every 1.5 months, 2 months, 3 months, 4 months, 5 months, or even 6 months).

As discussed hereinabove, some of the limitations for using presently known aminoglycosides as truncation mutation readthrough drugs are associated with the fact that they are primarily antibacterial (used as antibiotic agents). Chronic use of any antibacterial agents is highly unwarranted and even life threatening as it alters intestinal microbial flora which may cause or worsen other medical conditions such as flaring of inflammatory bowel disease, and may cause the emergence of resistance in some pathological strains of microorganisms.

In some embodiments, the compounds presented herein have substantially no antibacterial activity. By "no antibacterial activity" it is meant that the minimal inhibition concentration (MIC) thereof for a particular strain is much higher than the concentration of a compound that is considered an antibiotic with respect to this strain. Further, the MIC of these compounds is notably higher than the concentration required for exerting truncation mutation suppression activity.

Being substantially non-bactericidal, the compounds presented herein do not exert the aforementioned adverse effects and hence can be administered via absorption paths that may contain benign and/or beneficial microorganisms that are not targeted and thus their preservation may even be required. This important characteristic of the compounds presented herein renders these compounds particularly effective drugs against chronic conditions since they can be administered repetitively and during life time, without causing any antibacterial-related adverse, accumulating effects, and can further be administered orally or rectally, i.e. via the GI tract, which is a very helpful and important characteristic for a drug directed at treating chronic disorders.

According to some embodiments, the compounds presented herein are selected and/or designed to be selective towards the eukaryotic cellular translation system versus that of prokaryotic cells, namely the compounds exhibit higher activity in eukaryotic cells, such as those of mammalian (humans) as compared to their activity in prokaryotic cells, such as those of bacteria. Without being bound by any particular theory, it is assumed that the compounds presented herein, which are known to act by binding to the A-site of the 16S ribosomal RNA while the ribosome is involved in translating a gene, have a higher affinity to the eukaryotic ribosomal A-site, or otherwise are selective towards the eukaryotic A-site, versus the prokaryotic ribosomal A-site, as well as the mitochondrial ribosomal A-site which resembles its prokaryotic counterpart.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is expected that during the life of a patent maturing from this application many relevant genetic diseases and disorders as defined herein will be uncovered and the scope of this term is intended to include all such new disorders and diseases a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Chemical Syntheses of Exemplary Compounds Encompassed by the Present Embodiments In general, aminoglycosides (AGs) antibiotic are charged at physiological pH, thus they may be limited in their absorption through the GI tract and are therefore typically administered by injection. In addition, AGs exhibit limited permeability into eukaryotic cells, which requires their administration in higher dosages in order to overcome the cellular uptake limitation, which in turn causes adverse effects and limits their use in translational therapy. The compounds described in this example are designed in order to solve these problems.

To mitigate the GI tract absorption problem, alkyl/aryl groups are attached on the pseudo-trisaccharide scaffold at the N1 position of a paromamine-derived aminoglycoside.

To mitigate the cellular uptake limitation, a series of compounds is prepared with cell-permeablizable groups so as to increase their cellular uptake. These compounds are prepared by introducing a cell-permeablizable group, such as a guanidine group, at various positions on the scaffold.

The general synthetic pathway for preparing the compounds as described herein is described hereinabove, and generally is effected by coupling a suitable acceptor molecules and a suitable donor molecule, and de-protecting the protected hydroxyl and amino groups, to thereby obtain the desired compound.

The following presents processes for preparing exemplary acceptor molecules according to some embodiments of the present invention.

Preparation of Donor 1:

Donor 1 is suitable for preparing compounds having Formula I in which $R_8$ is guanidine, and the stereoconfiguration at position 5" is S.

Donor 1 is prepared as described in Med. Chem. Comm., 2011, 2, 165-171, and depicted in Scheme 1 below.

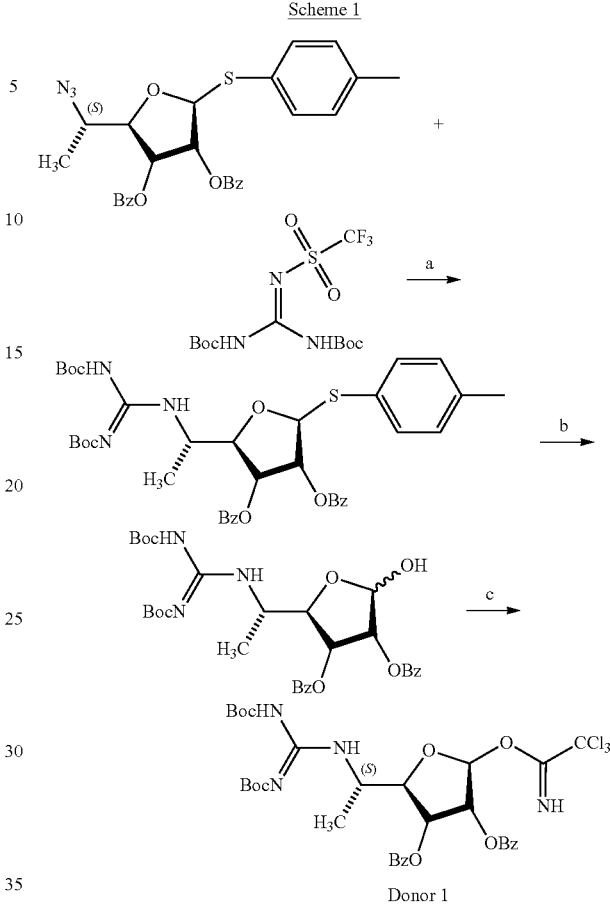

Scheme 1

Reagents and Conditions:

(a) $H_2$, Pd/C, DIPEA (b) NBS, Acetone/$H_2O$, −25° C. (c) $CCl_3CN$, $K_2CO_3$, 0° C., 25° C.

Preparation of Acceptors 1 and 2:

Acceptors 1 and 2 are prepared as described in Bioorg. Med. Chem., 2010, 18, pp. 3735-3746.

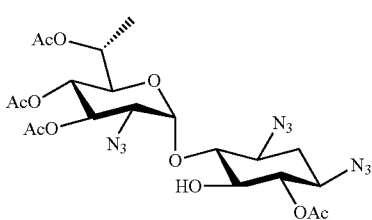

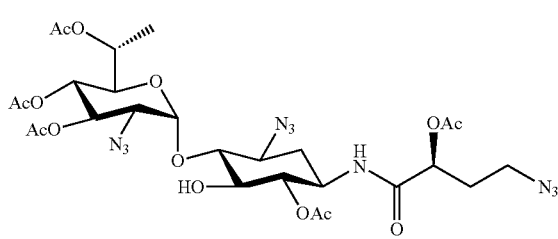

Preparation of Compounds D2 and E2:

Compounds D2 and E2 are prepared by coupling Donor 1 and Acceptors 1 and 2, respectively. The compound's structure is verified by, for example, NMR.

Preparation of Donor 2:

Donor 2 is prepared as described, for example, in WO 2012/066546. The donor is readily accessible from the known thioglycoside Compound 7 as illustrated in Scheme 2 below, wherein "a" represents 1,1-dimethoxypropane, CSA, acetone, room temperature; "b" represents Dess-Martin periodinane (DMP), DCM, room temperature; "c" represents MeMgBr, THF, −30° C.; "d" represents TsCl, Py, 4-DMAP, room temperature; "e" represents NaN3, HMPA, DMF, 70° C.; "f" represents acetic acid/water (8:2), reflux; "g" represents BzCl, Py, 4-DMAP, room temperature; "h" represents NBS, acetone/water (8:2), −30° C.; and "I" represents CCl3CN, DBU, DCM, 0° C.).

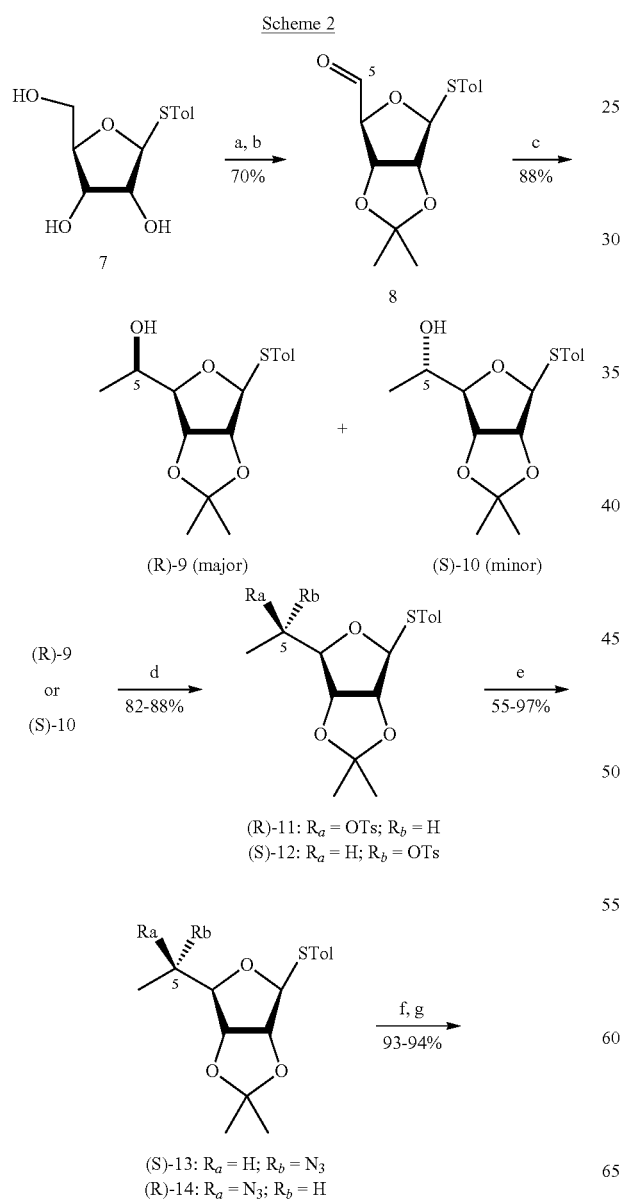

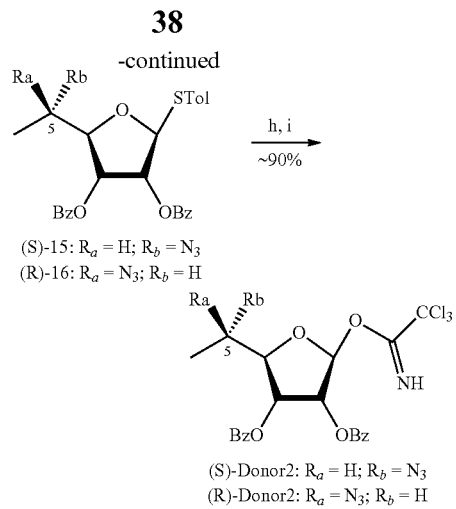

In Donor 2, CRaRb represents moiety D in Formula III, in which one of $R_6$ and $R_7$ is an amino-protected group (azido).

Preparation of Acceptor 3:

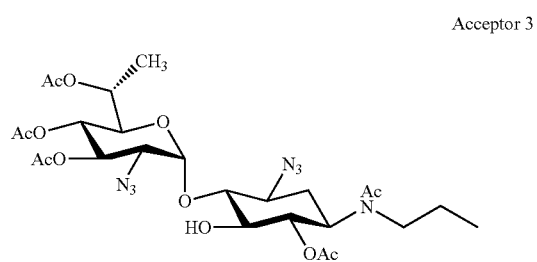

Acceptor 3 is prepared by selectively acylating Compound 2 (see, Scheme 3 below), and Compound 2 is prepared from Compound 1, prepared as previously reported in Baasov et al., *Bioorg. Med. Chem.*, 2010, 18, pp. 3735-3746.

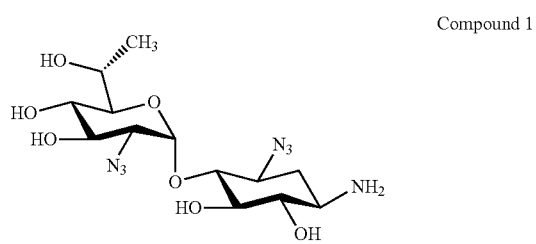

Compound 1 (0.5 grams, 1.2 mmol) was dissolved and stirred in water (15 mL) at 0° C. for 15 minutes and a 1 M solution of hydrochloric acid was added dropwise to adjust the pH of the reaction mixture to about 2-3. About 2 equivalents of propyl aldehyde (0.2 mL) were added to the reaction mixture and stirred for 15 minutes at room temperature. The resulted solution was cooled to 0° C. and NaBCNH3 (30 mg, 1.5 equivalents) was added and progress was monitored by TLC. After 1 hour of reaction, the similar process was repeated until starting material was consumed to desired product. After completion, the reaction mixture was evaporated and subjected to column chromatography to obtain Compound 2 in 0.325 gram (58%).

Compound 2 (750 mg, 1.0 equivalents) is dissolved in anhydrous pyridine (8 mL) and cooled to −20° C. At this temperature, acetic anhydride (2.0 mL, 5.6 equivalents) is added dropwise and the reaction is allowed to progress at −20° C. The reaction progress is monitored by TLC. Once completed, the reaction mixture is diluted with EtoAc, and extracted with aqueous solution of NaHCO$_3$, HCl (2%), saturated aqueous NaHCO$_3$, and brine. The combined organic layers are dried over anhydrous MgSO$_4$ and concentrated. The crude product is purified by silica gel column chromatography to afford Acceptor 3.

Preparation of Compound A2:

Compound A2 is prepared by coupling Acceptor 3 and Donor 2, as depicted in Scheme 3.

Scheme 3

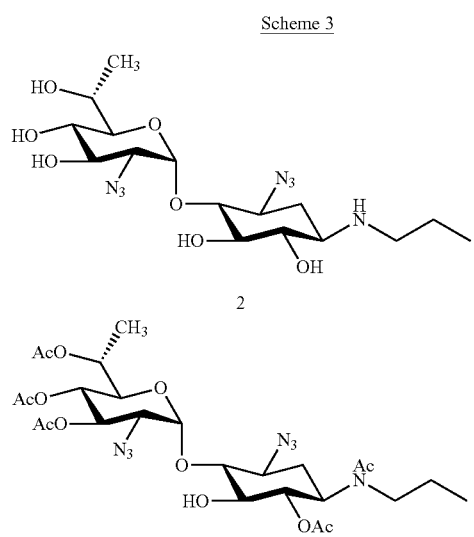

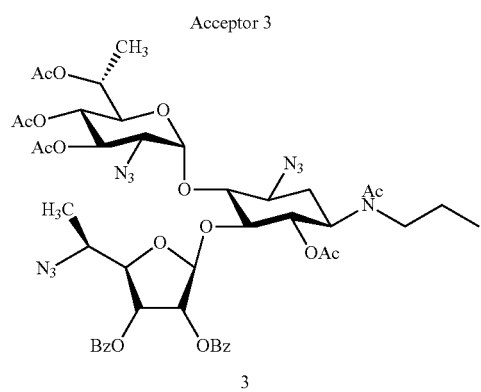

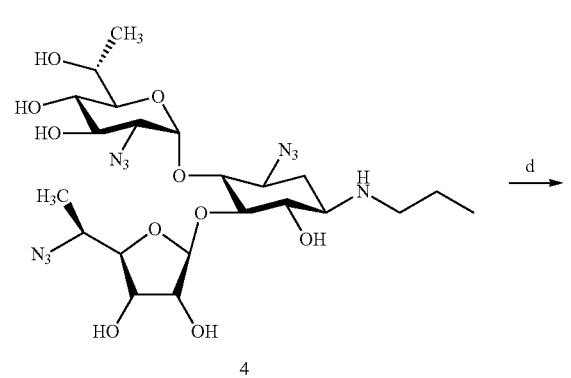

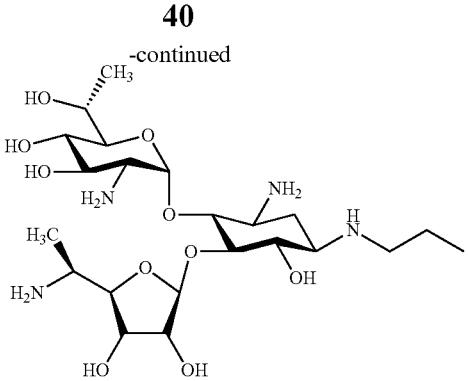

Compound A2

Reagents and conditions: a) 5.5 equivalents AC$_2$O, Py, -20° C., 24 hours; b) BF•OEt2, MS, CH$_2$Cl$_2$, -30° C., 3 h; c) THF, 0.5M NaOH, 60° C., 24 h; d) PMe$_3$, NaOH, THF, room temperature)

Preparation of Compounds B2 and C2:

Compounds B2 and C2 are similarly prepared, by coupling Donor 2 to Acceptors 4 and 5, respectively.

Acceptor 4

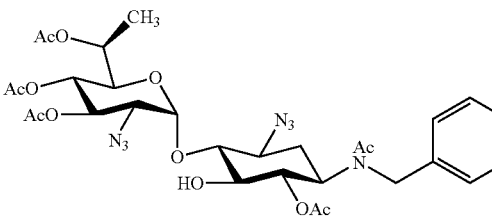

Acceptor 5

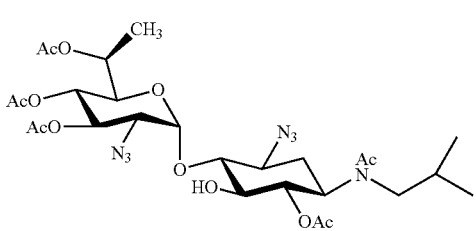

Acceptors 4 and 5 are prepared by preparing from Compound 1 suitable starting materials, corresponding to Compound 2. Thus, Compound 1 is reacted with benzaldehyde or isobutylaldehyde and the resulting compounds are further reacted to provide Acceptors 4 and 5, as described herein for Compound 2 and Acceptor 3.

Example 2

Readthrough Activity in Cell-Based Assay

Suppression of nonsense mutations (readthrough activity) by the compounds according to embodiments of the present invention is tested in vitro using reporter plasmids harboring a mutation in the chosen gene, as described, for example, in U.S. Pat. No. 8,895,519 and by Vecsler, M. et al. [*PLoS ONE*, 2011, 6(6) p. e20733].

Briefly, HEK-293T cells are transfected by the plasmids, and 24 hours post transfection the cells are lysed and tested for the expression levels of the firefly luciferase and renilla luciferase. Wild-type (WT) plasmids express both firefly luciferase and renilla luciferase while mutant plasmids only express the renilla luciferase due to the stop codon found in the inserted sequence. In the tested compounds' readthrough activity assays, the compounds are added to the cells' suspension 6 hours post-transfection. In case the compounds exert suppression of the premature nonsense/stop codon mutation, the firefly luciferase is expressed and a fold-change in its expression is observed.

To determine whether the tested compounds can induce the functional suppression of disease-causing nonsense mutations in human cells, the synthesis of firefly luciferase and renilla luciferase from cDNAs containing naturally occurring premature stop codon mutations that cause Rett syndrome are assayed. In all cases, the mutations introduce an in-frame ochre (UGA) stop codon in place of arginine residue, R168X, R270X and R294X mutations, which result in UGAG, UGAA and UGAU tetranucleotide termination signals, respectively.

Readthrough activity of Rett syndrome mutations is tested using the compounds described herein, and the mutation suppression is calculated based on firefly/renilla ratio values, normalized with the same ratio obtained without a tested compound (control), and compared to the expression levels observed in the WT. In general, since the renilla reporter gene is situated upstream with respect to the tested gene, and the firefly reporter gene is situated downstream, readthrough activity can be quantified by calculating the ratio of downstream expression to upstream expression (firefly/renilla expression ratio) and noting the proportion (percent) of this ratio with respect to the same measurements using the WT sequence, namely as normalized fractions of the expression level ratio observed for the WT. Alternatively, the firefly/renilla expression ratio can be normalized with respect to the firefly/renilla expression ratio observed in the control experiment (no readthrough-inducing compound). Since the firefly/renilla expression ratio in the WT is essentially insensitive to the presence of the readthrough-inducing compound, and the control experiment is essentially also insensitive to the presence of the readthrough-inducing compound, as none is present, the two normalization methods are expected to show similar trends, as seen in the results presented hereinbelow.

Measuring the same firefly/renilla expression ratios using the same compounds and control, but using the WT sequence, will signify the effect of the tested compounds on general expression level, regardless of the readthrough activity, thereby indicating if the tested compound exerts protein synthesis inhibition activity, as typical aminoglycoside antibiotics do. The WT measurements are also indicative of the experimental error.

Hence, if a given readthrough-inducing compound, according to some embodiments of the present invention, exerts some readthrough activity, the measurements will show a large firefly/renilla expression ratio compared to the firefly/renilla expression ratio observed for the control (no readthrough-inducing compound), and a high proportional value (in the order of hundreds percent). If there is no readthrough activity, the firefly/renilla expression ratios for both the inactive compound and the control are expected to be small absolutely and similar proportionally, giving a value of about 100%.

Example 3

Readthrough Activity in Cell-Free Assay

The plasmids are transcribed in vitro and translated using rabbit reticulocytes (TNT mix) and then tested for the expression levels of the firefly and renilla luciferases. WT plasmids express both firefly and renilla luciferases while mutant plasmids expressed only the renilla luciferase due to the stop codon found in the inserted sequence. The readthrough assays are conducted for the tested compounds and the controls by adding the compounds to the in vitro transcription/translation reaction mixture. In case the compounds exert suppression of the premature nonsense/stop codon mutation, the firefly luciferase is expressed and a fold-change in its expression is observed.

Readthrough activity of Cystic Fibrosis (CF) mutation G542X is tested using the compounds presented herein, and the mutation suppression is calculated based on firefly/renilla expression ratio values, and normalized with respect to the expression level of the WT and the control sample (no tested compound).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A compound represented by general Formula I:

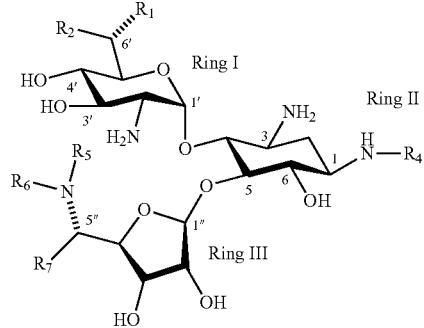

Formula I or a pharmaceutically acceptable salt thereof,
wherein:
the dashed lines indicates a stereo-configuration of position 6' being an R configuration or an S configuration;
$R_1$ is selected from hydrogen, alkyl, cycloalkyl or aryl;
$R_2$ is selected from a substituted or unsubstituted alkyl, OR' and NR'R", wherein each of R' and R" is independently selected from hydrogen, a substituted or unsubstituted alkyl, a substituted or unsubstituted cycloalkyl, a substituted or unsubstituted aryl, a substituted or unsubstituted heteroaryl, a substituted or unsubstituted alkaryl, and an acyl;
$R_4$ is selected from hydrogen, acyl, an amino-substituted alpha-hydroxy acyl, a substituted or unsubstituted alkyl, a substituted or unsubstituted cycloalkyl, a substituted or unsubstituted aryl, a substituted or unsubstituted alkaryl, and a cell-permealizable group;

$R_5$ and $R_6$ are each independently selected from hydrogen, a substituted or unsubstituted alkyl, a substituted or unsubstituted cycloalkyl, a substituted or unsubstituted aryl, a substituted or unsubstituted alkaryl, a substituted or unsubstituted heteroaryl, acyl, and a cell-permealizable group, or, alternatively, $R_5$ and $R_6$ form together a heterocyclic ring; and $R_7$ is alkyl, cycloalkyl or aryl, provided that:

when $R_2$ is hydroxy, $R_4$ is not hydrogen, AHB or AHP, and/or at least one of $R_5$ and/or $R_6$, if present, is not hydrogen.

2. The compound of claim 1, wherein $R_7$ is alkyl.

3. The compound of claim 1, wherein $R_7$ is methyl.

4. The compound of claim 1, wherein $R_1$ is alkyl.

5. The compound of claim 4, wherein said alkyl is methyl.

6. The compound of claim 1, wherein $R_1$ is hydrogen.

7. The compound of claim 1, wherein $R_2$ is OR'.

8. The compound of claim 7, wherein R' is hydrogen.

9. The compound of claim 4, wherein $R_2$ is OR'.

10. The compound of claim 9, wherein R' is hydrogen.

11. The compound of claim 6, wherein $R_2$ is OR'.

12. The compound of claim 11, wherein R' is hydrogen.

13. The compound of claim 1, wherein $R_4$ is selected from hydrogen, a substituted or unsubstituted alkyl, a substituted or unsubstituted cycloalkyl, a substituted or unsubstituted alkaryl, a substituted or unsubstituted acyl and an amino-substituted alpha-hydroxy acyl.

14. The compound of claim 1, wherein $R_4$ is a substituted or unsubstituted alkyl.

15. The compound of claim 1, wherein $R_5$ and $R_6$ are each hydrogen.

16. The compound of claim 1, wherein one of $R_5$ and $R_6$ is said cell-permealizable group.

17. The compound of claim 13, wherein $R_5$ and $R_6$ are each hydrogen.

18. The compound of claim 13, wherein one of $R_5$ and $R_6$ is said cell-permealizable group.

19. The compound of claim 18, wherein said cell-permealizable group is selected from guanidinyl and guanyl.

20. The compound of claim 1, wherein one of $R_5$ and $R_6$ is a guanidinyl.

21. The compound of claim 13, wherein one of $R_5$ and $R_6$ is a guanidinyl.

22. A pharmaceutical composition comprising the compound of claim 1 and a pharmaceutically acceptable carrier.

23. A method of substantially inhibiting, slowing or reversing the progression of, substantially ameliorating clinical or aesthetical symptoms of, or substantially preventing the appearance of clinical or aesthetical symptoms of a genetic disorder associated with a premature stop codon mutation in a subject suffering from said genetic disorder, the method comprising administering to the subject a therapeutically effective amount of the compound of claim 1.

24. The method of claim 23, wherein said genetic disorder is selected from the group consisting of cystic fibrosis (CF), Duchenne muscular dystrophy (DMD), ataxia-telangiectasia, Hurler syndrome, hemophilia A, hemophilia B, Usher syndrome, Tay-Sachs Becker muscular dystrophy (BMD), Congenital muscular dystrophy (CMD), Factor VII deficiency, Familial atrial fibrillation, Hailey-Hailey disease, McArdle disease, Mucopolysaccharidosis, Nephropathic cystinosis, Polycystic kidney disease, Rett syndrome, Spinal muscular atrophy (SMA), X-linked nephrogenic diabetes insipidus (XNDI) and X-linked retinitis pigmentosa.

* * * * *